(12) United States Patent
Chotani et al.

(10) Patent No.: US 8,980,598 B2
(45) Date of Patent: Mar. 17, 2015

(54) DRY SOLIDS STAGING FERMENTATION PROCESS

(75) Inventors: Gopal Chotani, Palo Alto, CA (US); Gang Duan, Singapore (SG); Craig E. Pilgrim, Beloit, WI (US); Jayarama K. Shetty, Palo Alto, CA (US)

(73) Assignee: Danisco US Inc., Palo Alto, CA (US)

( * ) Notice: Subject to any disclaimer, the term of this patent is extended or adjusted under 35 U.S.C. 154(b) by 952 days.

(21) Appl. No.: 11/151,919

(22) Filed: Jun. 14, 2005

(65) Prior Publication Data

US 2006/0281157 A1    Dec. 14, 2006

(51) Int. Cl.
*C12P 7/14*     (2006.01)
*C12P 7/06*     (2006.01)
*C12P 7/02*     (2006.01)

(52) U.S. Cl.
CPC ... *C12P 7/14* (2013.01); *Y02E 50/17* (2013.01)
USPC ............................. 435/162; 435/161; 435/155

(58) Field of Classification Search
None
See application file for complete search history.

(56) References Cited

U.S. PATENT DOCUMENTS

| 4,564,595 A * | 1/1986 | Neves ............................ 435/163 |
| 5,231,017 A * | 7/1993 | Lantero et al. ................. 435/161 |
| 5,837,506 A * | 11/1998 | Lynd et al. ..................... 435/165 |
| 2003/0180897 A1* | 9/2003 | Ulrich et al. ................... 435/134 |
| 2003/0180900 A1* | 9/2003 | Lantero .......................... 435/160 |

FOREIGN PATENT DOCUMENTS

| DE | 212 953 | 8/1984 |
| FR | 2550420 | * 2/1985 ................ A23J 1/12 |
| WO | WO 2004/081193 | 9/2004 |

OTHER PUBLICATIONS

Maria R. Castillo, Marcel Gutierrez-Correa, James C. Linden, Robert P. Tengerdy, Mixed culture solid substrate fermentation for cellulolytic enzyme production, Biotechnology Letters, vol. 16, Issue 9, Sep. 1994, pp. 967-972.*
Bransby D.I., Sladden S.E., Kee D.D., Selection and Improvement of Herbaceous Energy Crops for the Southeastern USA, Final Report on a Field and Laboratory research Program for the period of Mar. 15, 1985 to Mar. 14, 1990. USDOE and Oak Ridge National Laboratory, ORNL/Sub/85-27409/5.*
Juge, Nathalie; Le Gal-Coeffet,Marie-Francoise; Furniss, Caroline S. M.; Gunning, A. Patrick; Kramhoft, Birte; Morris, Vic J.; Williamson, Gary; Svensson, Birte, The starch binding domain of glucoamylase from *Aspergillus niger*: overview of its structure, function, and role in raw-starch hydrolysis,Biologia (Bratislava, Slovakia) 54, (2002), 239-245.*
Sorimachi, Kay; Le Gal-Coeffet, Marie-Francoise; Williamson, Gary; Archer, David B.; Williamson, Michael P.Solution structure of the granular starch binding domain of *Aspergillus niger* glucoamylase bound to beta-cyclodextrin, Structure (London) (1997), 5(5), 647-661.*
Belyea, R. L.; Rausch, K. D.; Tumbleson, M. Composition of corn and distillers dried grains with solubles from dry grind ethanol processing, Bioresource Technology (2004), 94(3), 293-298.*
Lewis, Richard J., Sr. (2002). Hawley's Condensed Chemical Dictionary (14th Edition). John Wiley & Sons. Online version available at: http://www.knovel.com/knovel2/Toc.jsp?BookID=704&VerticalID=0, last accessed May 10, 2006.*
Plimmer, Jack R.; Gammon, Derek W.; Ragsdale, Nancy N. Encyclopedia of Agrochemicals, vols. 1-3. John Wiley & Sons. Online version available at: http://www.knovel.com/knovel2/Toc.jsp?BookID=964&VerticalID=0,last accessed May 10, 2006.*
Aoki, Hiroyoshi; Sakano, Yopi; Sakano, Yoshiyuki, Molecular cloning and heterologous expression of the isopullulanase gene from *Aspergillus niger* A.T.C.C. 9642, Biochemical Journal (1997), 323(3), 757-764.*
Liu, Fang; Li, Wenqing; Ridgway, Darin; Gu, Tingyue; Moo-Young, MurrayInhibition of extracellular protease secretion by *Aspergillus niger* using cell immobilization, Biotechnology Letters (1998), 20(6), 539-542.*
American Type Culture Collection (ATCC), P.O. Box 1549, Manassas, VA 20108, USA,(2004) http://web.archive.org/web/20040612163104/http://www.atcc.org/ Last accessed May 10, 2006.*
U.S. Department of Energy, Biomass Feedstock Composition and Property Database http://www1.eere.energy.gov/biomass/feedstock_databases.html Last accessed May 30, 2006.*
Xu et al."Combined Use of Three Methods for High Concentration Ethanol Production by *Saccharomyces Cerevisiae*" Biotechnology Letters, vol. 18, No. 12, p. 1439.*
6. P. Longobardi "Fed-batch versus batch fermentation" Bioprocess Engineering 10 (1994) 185-194.*
S. W. Brown, S. G. Oliver, D. E. F. Harrison, and R. C. Righelato "Ethanol Inhibition of Yeast Growth and Fermentation: Differences in the Magnitude and Complexity of the Effect" European J Appl Microbiol Biotechnol (1981) 11:151-155.*
Xu et al. "Combined use of three methods for high concentration ethanol production by *Saccharomyces cerevisiae*" Biotechnology Letters, Dec. 1996, vol. 18, Issue 12, pp. 1439-1440.*
Ueda et al., "Production of Ethanol from Raw Cassava Starch by a Nonconventional Fermentation Method," *Biotechnolofy and Bioengineering*, V. XXIII, pp. 291-299 (1981).
PCT search report, Dec. 20, 2006, 6 pgs.

* cited by examiner

*Primary Examiner* — Thane Underdahl
(74) *Attorney, Agent, or Firm* — Danisco US Inc.

(57) ABSTRACT

A dry solids staging fermentation process for producing an end-product, such as ethanol is disclosed said process including an initial fermentation step including combining a first fermentable substrate with one or more starch hydrolyzing enzymes and fermenting organisms in a fermentation vessel and a loading step which includes adding a second fermentable substrate to the fermentation vessel wherein the percent dry solids (% DS) of the fermentation broth increases over time.

22 Claims, 6 Drawing Sheets

(SEQ. ID NO: 1)

```
AAVDTFINTEKPIAWNKLLANIGPNGKAAPGAAAGVVIASPSRTD
PPYFFTWTRDAALVLTGIIESLGHNYNTTLQTVIQNYVASQAKLQ
QVSNPSGTFADGSLGEAKFNVDLTAFTGEWGRPQRDGPPLRAIA
LIQYAKWLIANGYKSTAKSVVWPVVKNDLAYTAQYWNETGFDLWE
EVPGSSFFTIASSHRALTEGAYLAAQLDTECRACTTVAPQVLCFQ
QAFWNSKGNYVVSNINGGEYRSGKDANSILASIHNFDPEAGCDNL
TFQPCSERALANHKAYVDSFRNLYAINKGIAQGKAVAVGRYSEDV
YYNGNPWYLANFAAAEQLYDAIYVWNKQGSITVTSVLPFFRDLV
SSVSTGTYSKSSSTFTNIVNAVKAYADGFIEVAAKYTPSNGALAE
QYDRNTGKPDSAADLTWSYSAFLSAIDRRAGLVPPSWRASVAKSQ
LPSTCSRIEVAGTYVAATSTSFPSKQTPNPSAAPSPSPYPTACAD
ASEVYVTFNERVSTAWGETIKVVGNVPALGNWDTSKAVTLSASGY
KSNDPLWSITVPIKATGSAVQYKYIKVGTNGKITWESDPNRSITL
QTASSAGKCAAQTVNDSWR
```

FIG. 3

(SEQ. ID NO: 2)

```
ATLDSWLSNEATVARTAILNNIGADGAWVSGADSGIVVASPSTDN
PDYFYTWTRDSGLVIKTLVDLFRNGDTDLLSTIEHYISSQAIIQG
VSNPSGDLSSGGLGEPKFNVDETAYTGSWGRPQRDGPALRATAMI
GFGQWLLDNGYTSAATEIVWPLVRNDLSYVAQYWNQTGYDLWEEV
NGSSFFTIAVQHRALVEGSAFATAVGSSCSWCDSQAPQILCYLQS
FWTGSYILANFDSSRSGKDTNTLLGSIHTFDPEAGCDDSTFQPCS
PRALANHKEVVDSFRSIYTLNDGLSDSEAVAVGRYPEDSYYNGNP
WFLCTLAAAEQLYDALYQWDKQGSLEITDVSLDFFKALYSGAATG
TYSSSSSTYSSIVSAVKTFADGFVSIVETHAASNGSLSEQFDKSD
GDELSARDLTWSYAALLTANNRRNSVVPPSWGETSASSVPGTCAA
TSASGTYSSVTVTSWPSIVATGGTTTTATTTGSGGVTSTSKTTTT
ASKTSTTTSSTSCTTPTAVAVTFDLTATTTYGENIYLVGSISQLG
DWETSDGIALSADKYTSSNPLWYVTVTLPAGESFEYKFIRVESDD
SVEWESDPNREYTVPQACGESTATVTDTWR
```

FIG. 4

(SEQ. ID NO: 3)

```
LSAAEWRTQSIYFLLTDRFGRTDNSTTATCNTGDQIYCGGSWQGI
INHLDYIQGMGFTAIWISPITEQLPQDTSDGEAYHGYWQQKIYNV
NSNFGTADDLKSLSDALHARGMYLMVDVVPNHMGYAGNGNDVDYS
VFDPFDSSSYFHPYCLITDWDNLTMVQDCWEGDTIVSLPDLNTTE
TAVRTIWYDWVADLVSNYSVDGLRIDSVEEVPDFFPGYQEAAGV
YCVGEVDNGNPALDCPYQKYLDGVLNYPIYWQLLYAFESSSGSIS
NLYNMIKSVASDCSDPTLLGNFIENHDNPRFASYTSDYSQAKNVL
SYIFLSDGIPIVYAGEEQHYSGGDVPYNREATWLSGYDTSAELYT
WIATTNAIRKLAISADSDYITYANDPIYTDSNTIAMRKGTSGSQI
ITVLSNKGSSGSSYTLTLSGSGYTSGTKLIEAYTCTSVTVDSNGD
IPVPMASGLPRVLLPASVVDSSSLCGGSGNTTTTTAATSTSKAT
TSSSSSAAATTSSSCTATSTTLPITFEELVTTTYGEEVYLSGSI
SQLGEWDTSDAVKLSADDYTSSNPEWSVTVSLPVGTTFEYKFIKV
DEGGSVTWESDPNREYTVPECGSGSGETVVDTWR
```

FIG. 5

DRY SOLIDS STAGING FERMENTATION PROCESS

FIELD OF THE INVENTION

The present invention provides means for the production of end products, such as alcohols (e.g. ethanol) and distillers dry grain solubles (DDGS) from fermentable substrates in a fermentative process.

BACKGROUND OF THE INVENTION

The commercial viability of producing ethanol as a fuel source from agricultural crops has generated renewed worldwide interest due to a variety of reasons which include continued and increased dependence on limited oil supplies and the fact that ethanol production is a renewable energy source.

Alcohol fermentation production processes and particularly ethanol production processes are generally characterized as wet milling or dry milling processes. Reference is made to Bothast et al., 2005, *Appl. Microbiol. Biotechnol.* 67:19-25 and THE ALCOHOL TEXTBOOK, $3^{rd}$ Ed (K. A. Jacques et al. Eds) 1999 Nottingham University Press, UK for a review of these processes.

In general, the wet milling process involves a series of soaking (steeping) steps to soften the cereal grain wherein soluble starch is removed followed by recovery of the germ, fiber (bran) and gluten (protein). The remaining starch is further processed by drying, chemical and/or enzyme treatments. The starch is then used for alcohol production, high fructose corn syrup or commercial pure grade starch.

In general dry grain milling involves a number of basic steps, which include: grinding, cooking, liquefaction, saccharification, fermentation and separation of liquid and solids to produce alcohol and other co-products. Generally, whole cereal, such as corn cereal, is ground to a fine particle size and then mixed with liquid in a slurry tank. The slurry is subjected to high temperatures in a jet cooker along with liquefying enzymes (e.g. alpha amylases) to solublize and hydrolyze the starch in the cereal to dextrins. The mixture is cooled down and further treated with saccharifying enzymes (e.g. glucoamylases) to produce fermentable glucose. The mash containing glucose is then fermented for approximately 24 to 120 hours in the presence of ethanol producing microorganisms. The solids in the mash are separated from the liquid phase and ethanol and useful co-products such as distillers' grains are obtained (FIG. 1A).

Improvements to the above fermentation processes have been accomplished by combining the saccharification step and fermentation step in a process referred to as simultaneous saccharification and fermentation or simultaneous saccharification, yeast propagation and fermentation. These improved fermentation processes have advantages over the previously described dry milling fermentation or even wet milling fermentation processes because significant sugar concentrations do not develop in the fermenter thereby avoiding sugar inhibition of yeast growth. In addition, bacterial growth is reduced due to lack of easily available glucose. Increased ethanol production may result by use of the simultaneous saccharification and fermentation processes.

More recently, fermentation processes have been introduced which eliminate the cooking step or which reduce the need for treating cereal grains at high temperatures. These no-cook or low temperature fermentation processes include milling of a cereal grain and combining the ground cereal grain with liquid to form a slurry which is then mixed with one or more granular starch hydrolyzing enzymes and optionally yeast to produce ethanol and other co-products (U.S. Pat. No. 4,514,496, WO 04/081193 and WO 04/080923) (FIG. 1B).

While no-cook or low temperature fermentation processes using a milled grain slurry in combination with granular starch hydrolyzing enzymes offers certain improvements over previous processes, the dry solids staging fermentation process of the instant invention provides further advantages for the production of alcohol and other end products. Some of these advantages include, but are not limited to:

a) elimination of a slurry or feed tank comprising substrates containing granular starch which feeds into a saccharification vessel;

b) decreases in the potential for microbial contamination in the fermentation of nonsterile granular starch containing substrates because of the elimination of a slurry step before the saccharification and fermentation;

c) improved mixing, faster hydration of the substrate, and improved carbon conversion efficiency because of a lower % DS in the starting mash of the initial fermentation;

d) overall high solids loading during the fermentation run;

e) an equal or higher ethanol concentration in the presence of residual starch levels which may be higher in other no-cook or low temperature fermentation processes of substrates containing granular starch, which are not subject to dry solids staging;

f) optional elimination of the yeast seed propagation tank;

g) reduced stress on yeast during the fermentation;

h) ability to handle a very fine milled substrate which will reduce the amount of residual starch, but will not result in adversely increasing the viscosity of the mash in the fermentation vessel; and i) an increase in the enzyme to fermentable substrate ratio which enhances the hydrolysis of starch.

SUMMARY OF THE INVENTION

In a first aspect, the invention pertains to a dry solids staging fermentation process for producing an end-product comprising an initial fermentation step which includes combining a first fermentable substrate with one or more starch hydrolyzing enzymes and a fermenting organism in a fermentation vessel at a pH of 3.0 to 7.0, a temperature of 5° C. to 65° C., for 2 to 40 hours and obtaining a fermentation broth and a loading step which includes adding a second fermentable substrate into the vessel which contains the fermentation broth and allowing continued fermentation at a pH of 3.0 to 7.0, a temperature of 20° C. to 65° C. for a sufficient period of time to produce an end-product, wherein the percent dry solids (% DS) of the fermentation broth increases over time.

In some embodiments of this aspect, the first fermentable substrate and the second fermentable substrate are the same and in other embodiments, the first fermentable substrate and the second fermentable substrate are different. In further embodiments, the fermentable substrate is a solid fermentable substrate and in additional embodiments the solid fermentable substrate is a dry ground cereal grain. In other embodiments of this aspect, the initial DS 0 to 40% DS and the accumulated DS is between 10 to 55%. In a further embodiment of this aspect, the loading step comprises addition of DS in increments of 1 to 20%. In yet further embodiments, the one or more starch hydrolyzing enzymes are selected from glucoamylases, alpha amylases, granular starch hydrolyzing enzymes and combinations thereof. In yet another embodiment, the end-product is an alcohol and the fermenting organism is a yeast.

In a second aspect, the invention pertains to a dry solids staging fermentation process for producing alcohol comprising an initial fermentation step which includes combining a fermentable substrate, one or more starch hydrolyzing enzymes and a fermenting organism in a fermentation vessel at a pH of 3.0 to 6.0, a temperature of 5° C. to 65° C. for 2 to 40 hours and obtaining a fermentation broth and a loading step which includes adding a solid fermentable substrate into the vessel containing the fermentation broth and allowing continued fermentation at a pH of 3.0 to 6.0, a temperature of 20° C. to 55° C. for a sufficient period of time to produce an alcohol, wherein the percent dry solids (% DS) of the fermentation broth increases over time.

In a third aspect, the invention pertains to a solid staging fermentation process for produces ethanol comprising an initial fermentations step which includes directly feeding a solid fermentable substrate into a fermentation vessel and combining the solid fermentable substrate with yeast and with one or more starch hydrolyzing enzymes selected from the group consisting of glucoamylases, alpha amylases, granular starch hydrolyzing enzymes and combinations thereof in the fermentation vessel at a pH of 3.0 to 6.5, a temperature of 20° C. to 55° C., for 2 to 40 hours and obtaining a fermentation broth and a loading step which includes directly feeding the solid fermentable substrate into the vessel which contains the fermentation broth and allowing fermentation of the substrate at a pH of 3.0 to 6.5, a temperature of 20° C. to 55° C. for a sufficient period of time to produce ethanol, wherein % DS of the fermentation broth increases over time. In some embodiments of this aspect, the solid fermentable substrate is a dry ground cereal grain. In further embodiments of this aspect, additional doses of the one or more starch hydrolyzing enzymes and/or yeast are added to the fermentation vessel during the loading step.

In a fourth aspect, the invention pertains to a method of increasing accumulated dry solids (DS) in a fermentation broth used for the production of alcohol comprising using the dry solids staging fermentation process encompassed by the invention.

In a fifth aspect, the invention concerns a means of reducing bacterial contamination during the fermentation of a fermentable substrate. One embodiment of this aspect comprises the direct feeding of a solid fermentable substrate, such as a dry ground cereal grain, into a fermentation vessel during the dry solids staging fermentation process encompassed by the invention.

BRIEF DESCRIPTION OF THE DRAWINGS

FIG. 1A illustrates a conventional dry milling alcohol fermentation process, which includes subjecting a slurry of a substrate containing granular starch to a high temperature liquefaction step prior to saccharification and fermentation;

FIG. 3 provides the mature amino acid sequence (SEQ ID NO: 1) for a glucoamylase of *Humicola grisea* var. *thermoidea* having GSH activity.

FIG. 4 provides the mature amino acid sequence (SEQ ID NO: 2) for a glucoamylase of *Aspergillus awamori* var. *kawachi* having GSH activity.

FIG. 5 provides the mature amino acid sequence (SEQ ID NO: 3) for an alpha amylase of *Aspergillus kawachi* having GSH activity.

DETAILED DESCRIPTION OF THE INVENTION

Figure 1A:
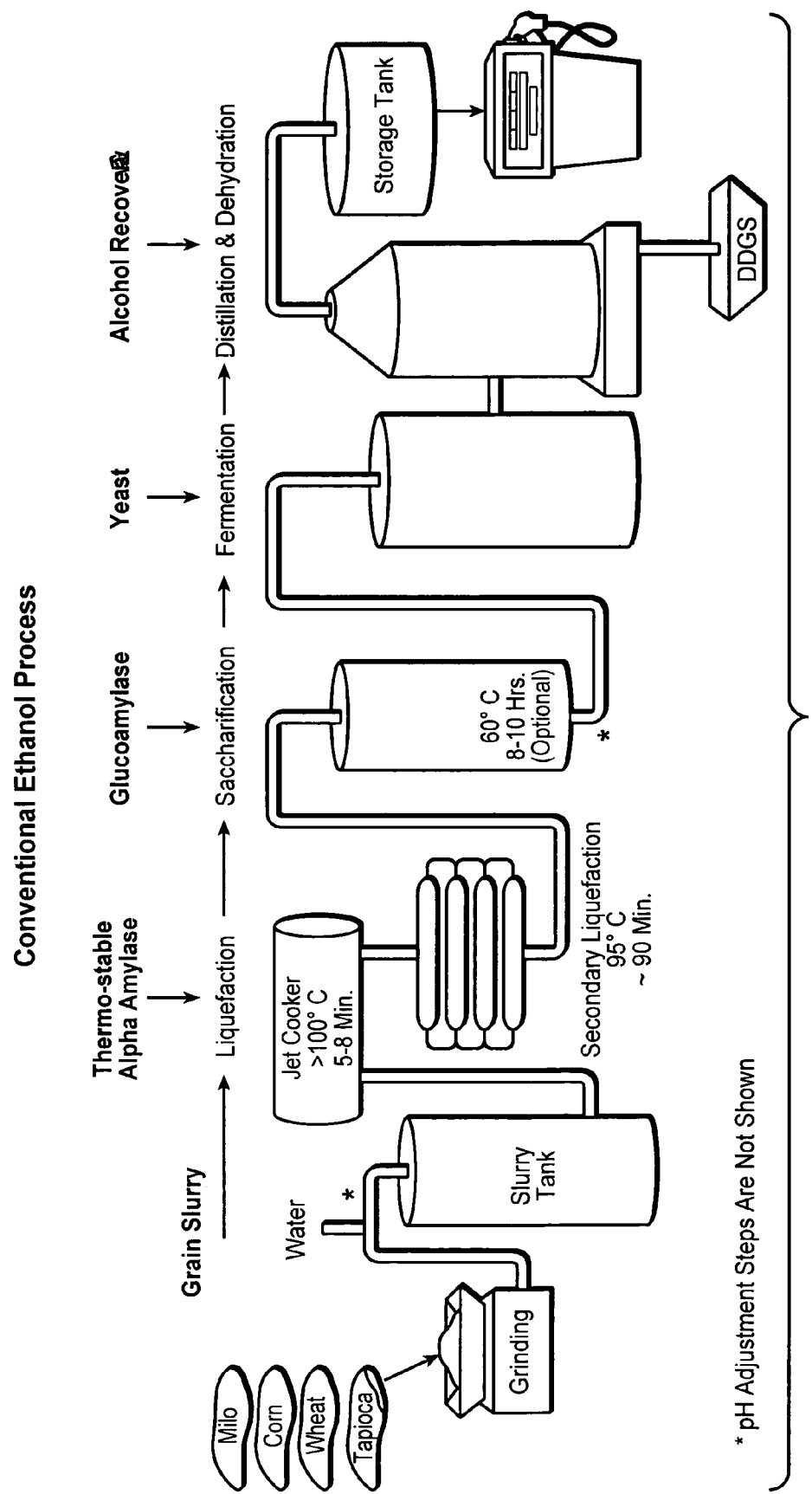
FIGS. 1A, B and C are general schematic diagrams which illustrate alcohol fermentation production processes.
Figure 1B:
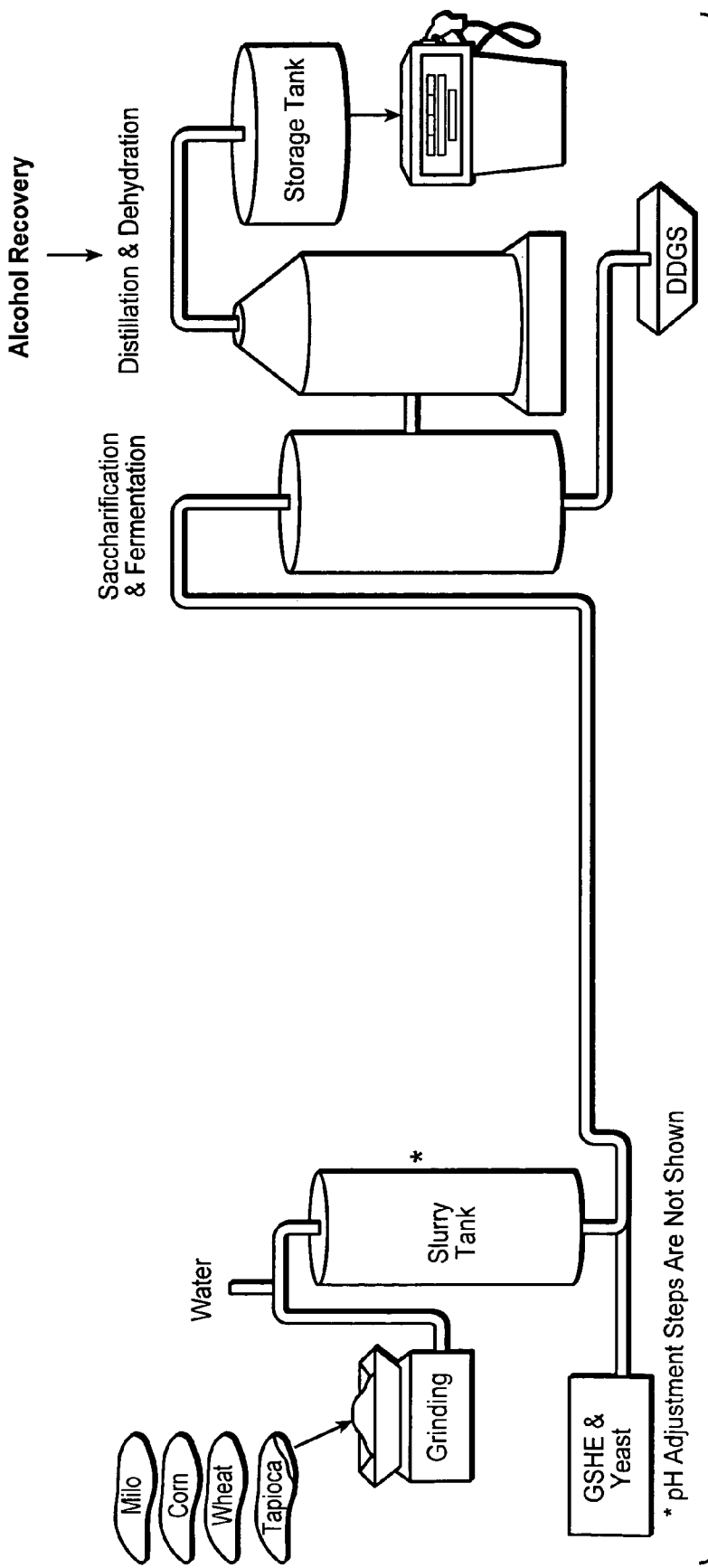
FIG. 1B illustrates a no-cook dry milling alcohol fermentation process, which includes combining a slurry of a substrate containing granular starch with granular starch hydrolyzing enzymes at a temperature below the gelatinization temperature of the granular starch of the substrate in a simultaneous saccharification and fermentation process.

Unless defined otherwise herein, all technical and scientific terms used herein have the same meaning as commonly understood by one of ordinary skill in the art to which this invention belongs.

Although any methods and materials similar or equivalent to those described herein can be used in the practice or testing of the present invention, the preferred methods and materials are described.

The invention will now be described in detail by way of reference only using the following definitions and examples. All patents and publications, including all sequences disclosed within such patents and publications, referred to herein are expressly incorporated by reference.

Definitions

The phrase "dry solids staging" refers to at least two steps in a fermentation process including an initial fermentation step and a loading step.

An "initial fermentation step" refers to combining a fermentable substrate with one or more starch hydrolyzing enzymes and a fermenting organism in a fermentation vessel under conditions suitable to start fermentation.

A "loading step" refers to the addition of fermentable substrates, after an initial fermentation step, to the fermentation vessel comprising one or more starch hydrolyzing enzymes and a fermenting organism and the continued fermentation of fermentable substrates.

The term "fermentation" refers to the enzymatic and anaerobic breakdown of organic substances by microorganisms to produce simpler organic compounds. While fermentation occurs under anaerobic conditions it is not intended that the term be solely limited to strict anaerobic conditions, as fermentation also occurs in the presence of oxygen.

The phrase "simultaneous saccharification and fermentation (SSF)" refers to a process in the production of end products in which a fermenting organism, such as an ethanol producing microorganism, and at least one enzyme, such as a saccharifying enzyme are combined in the same process step in the same vessel.

The term "saccharification" refers to enzymatic conversion of a directly unusable polysaccharide to a mono- or oligosaccharide for fermentative conversion to an end-product.

The term "fermentable substrate" refers to both carbon substrates, which can be enzymatically converted to a fermentable sugar and to fermentable sugars.

The term "carbon substrate" refers to cellulose, hemicellulose and/or starch containing plant based materials.

The term "solid fermentable substrate" refers to a fermentable plant based substrate that is substantially free of added water or other aqueous liquid.

The term "dry ground cereal grain" refers to a solid fermentable substrate which is a milled cereal grain having a moisture content of about between 2% to 25% on a dry weight basis.

The phrases "direct feeding of a solid fermentable substrate" or "directly feeding a solid fermentable substrate" refer to the transfer of the solid fermentable substrate, into the fermentation vessel without first being combined with an aqueous solution in a slurry or holding tank or the like. In some embodiments, direct feeding is the transfer of the solid fermentable substrate into the fermentation vessel without addition of added aqueous liquid, and in other embodiments, direct feeding includes an in-line feed means which combines the solid fermentable substrate with an aqueous liquid.

A "fermentable sugar" refers to mono- or disaccharides, which may be converted in a fermentation process by a microorganism in contact with the fermentable sugar to produce an end product. In some embodiments, the fermentable sugar is metabolized by the microorganism and in other embodiments the expression and/or secretion of enzymes by the microorganism achieves the desired conversion of the fermentable sugar.

As used herein, "monosaccharide" refers to a monomeric unit of a polymer such as starch wherein the degree of polymerization (DP) is 1 (e.g., glucose, mannose, fructose and galactose).

As used herein, "disaccharide" refers to any compound that comprises two covalently linked monosaccharide units (DP2). The term encompasses, but is not limited to such compounds as sucrose, lactose and maltose.

As used herein a DP>3 denotes polymers with a degree of polymerization of greater than 3.

As used herein, "oligsaccharide" refers to any compound having 2-10 monosaccharide units joined in glycosidic linkages.

As used herein, "polysaccharide" refers to any compound having multiple monosaccharide units joined in a linear or branched chain. In some embodiments the term refers to long chains with hundreds or thousands of monosaccharide units. Typical examples of polysaccharides are starch, cellulose and glycogen.

As used herein the term "starch" refers to any material comprised of the complex polysaccharide carbohydrates of plants, comprised of amylose and amylopectin with the formula $(C_6H_{10}O_5)_x$, wherein x can be any number.

The term "granular starch" refers to raw (uncooked) starch, e.g., granular starch that has not been subject to gelatinization.

The term "cellulose" refers to any cellulose-containing material. In particular, the term refers to the polymer of glucose (cellobiose) with the formula $(C_6H_{10}O_5)_x$, wherein x can be any number.

As used herein the term "dry solids content (DS)" refers to the total solids of a slurry in % on a dry weight basis.

The term "accumulated DS" refers to the total % DS added over a period of time in a fermentation process.

The term "initial DS" refers to the % DS in a fermentation medium or broth at the start of a fermentation process. In one embodiment, the initial DS refers to the % DS in the fermentation medium at the start of the initial fermentation step of the dry solids staging fermentation process of the invention.

The phrase "the percent dry solids (% DS) of the fermentation broth increases over time" refers to an accumulated DS that is greater than an initial DS due to addition of a fermentable substrate during the loading step. The increase may be accomplished by incremental, continuous or one time addition of the fermentable substrate.

The term "slurry" refers to an aqueous mixture containing insoluble solids, (e.g. granular starch).

The term "mash" refers to a mixture of a fermentable substrate in liquid used in the production of a fermented product and is used to refer to any stage of the fermentation from the initial mixing of the fermentable substrate with one or more starch hydrolyzing enzymes and fermenting organisms through the completion of the fermentation run. Sometimes the terms "mash", "slurry", "fermentation broth", "fermentation medium" and "beer" are used interchangeably. In some embodiments the term fermentation broth means a fermentation medium, which includes the fermenting organisms.

The term "milling" refers to the breakdown of cereal grains to smaller particles. In some embodiments the term is used interchangeably with grinding.

The term "dry milling" refers to the milling of dry whole grain, wherein fractions of the grain such as the germ and bran have not been purposely removed.

As used herein the terms "distillers dried grain (DDG)" and "distillers dried grain with solubles (DDGS)" refer to useful co-products of grain fermentation processes.

The term "residual starch" refers to the remaining starch (soluble and insoluble) left in a composition after fermentation of a starch containing fermentable substrate.

The terms "saccharifying enzyme" and "starch hydrolyzing enzymes" refer to any enzyme that is capable of converting starch to mono- or oligosaccharides.

The term "glucoamylase" refers to the amyloglucosidase class of enzymes (e.g., E.C.3.2.1.3, glucoamylase, 1,4-alpha-D-glucan glucohydrolase). These are exo-acting enzymes, which release glucosyl residues from the non-reducing ends of amylose and amylopectin molecules. The enzymes also hydrolyzes alpha-1,6 and alpha-1,3 linkages although at much slower rate than alpha-1,4 linkages.

The terms "granular starch hydrolyzing (GSH) enzyme" and "enzymes having granular starch hydrolyzing (GSH) activity" refer to enzymes, which have the ability to hydrolyze starch in granular form.

The term "hydrolysis of starch" refers to the cleavage of glucosidic bonds with the addition of water molecules.

The term "alpha-amylase (e.g., E.C. class 3.2.1.1)" refers to enzymes that catalyze the hydrolysis of alpha-1,4-glucosidic linkages. These enzymes have also been described as those effecting the exo or endohydrolysis of 1,4-α-D-glucosidic linkages in polysaccharides containing 1,4-α-linked D-glucose units. Another term used to describe these enzymes is "glycogenase".

The term "gelatinization" means solubilization of a starch molecule by cooking to form a viscous suspension.

The term "gelatinization temperature" refers to the lowest temperature at which gelatinization of a starch containing substrate begins. The exact temperature of gelatinization depends on the specific starch and may vary depending on factors such as plant species and environmental and growth conditions.

The term "below the gelatinization temperature" refers to a temperature which is less than the temperature that starts gelatinization.

The term "liquefaction" refers to the stage in starch conversion in which gelatinized starch is hydrolyzed to give low molecular weight soluble dextrins.

The term "thin-stillage" refers to the resulting liquid portion of a fermentation which contains dissolved material and suspended fine particles and which is separated from the solid portion resulting from the fermentation.

The term "vessel" includes but is not limited to tanks, vats, bottles, flasks, bags, bioreactors and the like. In one embodiment, the term refers to any receptacle suitable for conducting the saccharification and/or fermentation processes encompassed by the invention.

The term "end-product" refers to any carbon-source derived product which is enzymatically converted from a fermentable substrate. In some preferred embodiments, the end product is an alcohol, such as ethanol.

As used herein the term "fermenting organism" refers to any microorganism or cell which is suitable for use in a fermentation for directly or indirectly producing an end-product.

As used herein the term "ethanol producer" or ethanol producing microorganism" refers to a fermenting organism that is capable of producing ethanol from a mono- or oligosaccharide.

The term "ascorbic acid intermediate (ASA)" means any one of the following compounds: D-gluconate, 2-keto-D-gluconate (2KDG), 2,5-diketo-D-gluconate (2,5-DKG), 2-keto-L-gulonic acid (2KLG), erythorbic acid (EA) and ascorbic acid (ASA).

As used herein, "ascorbic acid intermediate producer" refers to a fermenting organism that is capable of producing an ASA intermediate from a monosaccharide.

As used herein, "glycerol producer" refers to a fermenting organism that is capable of producing glycerol from a monosaccharide.

As used herein, "diol producer" refers to a fermenting organism that is capable of producing 1,3-propanediol utilizing glycerol.

The term "derived" encompasses the terms "originated from", "obtained" or "obtainable from", and "isolated from" and in some embodiments as used herein means that a polypeptide encoded by the nucleotide sequence is produced from a cell in which the nucleotide is naturally present or in which the nucleotide has been inserted.

The term "heterologous protein" refers to a protein or polypeptide that does not naturally occur in a host cell. The term "endogenous protein" refers to a protein or polypeptide that does naturally occur in a host cell.

The term "enzymatic conversion" in general refers to the modification of a substrate by enzyme action. The term as used herein also refers to the modification of a fermentable substrate, such as a granular starch containing substrate by the action of an enzyme.

The terms "recovered", "isolated", and "separated" as used herein refer to a compound, protein, cell, nucleic acid or amino acid that is removed from at least one component with which it is naturally associated.

As used herein the term "specific activity" means an enzyme unit defined as the number of moles of substrate converted to product by an enzyme preparation per unit time under specific conditions. Specific activity is expressed as units (U)/mg of protein.

As used herein the term "enzyme unit" refers to the amount of enzyme that produces 1 micromole of product per minute under the specified conditions of the assay. For example, in one embodiment, the term "glucoamylase activity unit" (GAU) is defined as the amount of enzyme required to produce 1 g of glucose per hour from soluble starch substrate (4% DS) under assay conditions of 60° C. and pH 4.2.

The term "yield" refers to the amount of end-product produced using the methods of the present invention. In some embodiments, the term refers to the volume of the end-product and in other embodiments, the term refers to the concentration of the end-product.

The term "DE" or "dextrose equivalent" is an industry standard for measuring the concentration of total reducing sugars, calculated as D-glucose on a dry weight basis. Unhydrolyzed granular starch has a DE that is essentially 0 and D-glucose has a DE of 100.

The term "sugar syrup" refers to an aqueous composition containing soluble carbohydrates. In one embodiment, the sugar syrup is a syrup containing glucose.

As used herein the term "comprising" and its cognates are used in their inclusive sense; that is, equivalent to the term "including" and its corresponding cognates.

"A", "an" and "the" include plural references unless the context clearly dictates otherwise.

Numeric ranges are inclusive of the numbers defining the range.

The headings provided herein are not limitations of the various aspects or embodiments of the invention, which can be had by reference to the specification as a whole.

Raw Materials:
Fermentable Substrates

A fermentable substrate useful in the present invention includes both carbon substrates such as cellulose and starch containing plant based materials and sugars. Suitable plants include but are not limited to wheat, corn, rye, sorghum, rice, millet, barley, cassava, tapioca, potato, sweet potato, sugar beets, sugar cane, and legumes such as soybean and peas. Any part of the plant may be used as a fermentable substrate including but not limited to plant parts such as leaves, stems, hulls, husks, tubers, cobs, grains and the like. In some embodiments, essentially the entire plant may be used, for example, the entire corn stover may be used. In one preferred embodiment, whole grain is used as the fermentable substrate. Preferred whole grains include corn, wheat, rye, barley and sorghum (milo). In addition, corn hybrids, which have been developed for enhanced ethanol production also find use in the process of the invention. These hybrids may be characterized by high total fermentable and/or high extractable starch. Additionally, fermentable cereal grain substrates may be fractionated into various parts including fiber, endosperm and/or germ prior to fermentation. Methods for fractionating plant material such as corn and wheat are known in the art.

In some embodiments, the fermentable substrate containing granular starch may be highly refined raw starch or feedstock from starch refinery processes. Various starches are commercially available. For example, cornstarches are available from Cerestar, Sigma, and Katayama Chemical Industry Co. (Japan); wheat starches are available from Sigma; sweet potato starches are available from Wako Pure Chemical Industry Co. (Japan); and potato starch is available from Nakaari Chemical Pharmaceutical Co. (Japan).

Those of general skill in the art are well aware of available methods which may be used to prepare plant substrates and particularly cereal grain for use in the methods encompassed by the invention. In some embodiments, the fermentable substrate may be prepared by means such as grinding. In particular means of milling whole cereal grains are known and include the use of hammer mills and roller mills.

In some embodiments of the process of the invention, a fermentable substrate and particularly a cereal grain is milled to a fine particle size, such that at least 80%, at least 85%, at least 90%, and at least 95% of the fermentable substrate will pass through a 0.5 mm screen (30 mesh number). In other embodiments, the cereal grain is milled to a coarse particle size such that less than 50%, less than 40%, less than 30% and less than 20% of the milled grain will pass through a 0.5 mm screen.

While in certain embodiments, preferred fermentable substrates are plants or plant parts comprising granular starch, in other embodiments, soluble forms of starch are used as the fermentable substrate. Soluble forms of starch include unpurified mixtures for renewable feedstocks such as corn syrup, molasses (such as sugar beet or sugar cane), barely malt, isoglucose, high fructose corn syrup and invert sugars.

In some embodiments, the fermentable substrate is a soluble sugar such as a monosaccharide and/or disaccharide. Monosaccharides include hexoses, such as glucose, mannose, idose and galactose and include pentoses, such as ribose, xylose and arabinose. Disaccharides include sucrose, lactose, maltose and cellobiose. In some embodiments, the fermentable sugar is glucose, fructose, sucrose or a combination thereof.

In some embodiments, the fermentable substrate comprises stillage which is a mixture of non-fermented solids and water which is the residue after removal of alcohol from a mash. In addition, the liquid portion of the stillage, known as thin stillage may be used as a fermentable substrate.

Other fermentable substrates include agricultural resides and lignocellulosic material such as corn stover, begasses, wood, wood chips, wood pulp and sawdust. Examples of paper waste include but are not limited to discarded paper of any type (e.g. photocopy paper, notebook paper), newspapers, cardboard and magazines.

Starch Hydrolyzing Enzymes:
Glucoamylases

Glucoamylases (GA) (E.C. 3.2.1.3.) may be derived from the heterologous or endogenous protein expression of bacteria, plants and fungi sources. Preferred glucoamylases useful in the compositions and methods of the invention are produced by several strains of filamentous fungi and yeast. In particular, glucoamylases secreted from strains of *Aspergillus* and *Trichoderma* are commercially important. Suitable glucoamylases include naturally occurring wild-type glucoamylases as well as variant and genetically engineered mutant glucoamylases. The following glucoamylases are nonlimiting examples of glucoamylases that may be used in the process encompassed by the invention. *Aspergillus niger* G1 and G2 glucoamylase (Boel et al., (1984) *EMBO J.* 3:1097-1102; WO 92/00381, WO 00/04136 and U.S. Pat. No. 6,352,851); *Aspergillus awamori* glucoamylases (WO 84/02921); *Aspergillus oryzae* glucoamylases (Hata et al., (1991) *Agric. Biol. Chem.* 55:941-949) and *Aspergillus shirousami*. (See Chen et al., (1996) *Prot. Eng.* 9:499-505; Chen et al. (1995) *Prot. Eng.* 8:575-582; and Chen et al., (1994) *Biochem J.* 302:275-281).

Glucoamylases are also obtained from strains of *Talaromyces* such as those derived from *T. emersonii, T. leycettanus, T. duponti* and *T. thermophilus* (WO 99/28488; U.S. Pat. No. RE 32,153; U.S. Pat. No. 4,587,215); strains of *Rhizopus*, such as *R. niveus* and *R. oryzae*; strains of *Mucor* and strains of *Humicola*, such as *H. grisea* (See, Boel et al., (1984) *EMBO J.* 3:1097-1102; WO 92/00381; WO 00/04136; Chen et al. (1996) *Prot. Eng.* 9:499-505; Taylor et al., (1978) *Carbohydrate Res.* 61:301-308; U.S. Pat. No. 4,514,496; U.S. Pat. No. 4,092,434; and Jensen et al., (1988) *Can. J. Microbiol.* 34:218-223). Other glucoamylases useful in the present invention include those obtained from *Athelia rolfsii* and variants thereof (WO 04/111218).

Enzymes having glucoamylase activity used commercially are produced for example, from *Aspergillus niger* (trade name DISTILLASE, OPTIDEX L-400 and G ZYME G990 4X from Genencor International Inc.) or *Rhizopus* species (trade name CU.CONC from Shin Nihon Chemicals, Japan). Also the commercial digestive enzyme, trade name GLUCZYME from Amano Pharmaceuticals, Japan (Takahashi et al., (1985) *J. Biochem.* 98:663-671). Additional enzymes include three forms of glucoamylase (E.C.3.2.1.3) of a *Rhizopus* sp., namely "Gluc1" (MW 74,000), "Gluc2" (MW 58,600) and "Gluc3" (MW 61,400). Also the enzyme preparation GC480 (Genencor International Inc.) finds use in the invention.

Alpha Amylases

In some of the embodiments encompassed by the invention, the alpha amylase is a microbial enzyme having an E.C. number, E.C. 3.2.1.1-3 and in particular E.C. 3.2.1.1. In some embodiments, the alpha amylase is a thermostable bacterial alpha amylase. In other embodiments, the alpha amylase is a acid stable alpha amylase. Suitable alpha amylases may be naturally occurring as well as recombinant and mutant alpha amylases. In particularly preferred embodiments, the alpha amylase is derived from a *Bacillus* species. Preferred *Bacillus* species include *B. subtilis, B. stearothermophilus, B. lentus, B. licheniformis, B. coagulans*, and *B. amyloliquefaciens* (U.S. Pat. No. 5,093,257; U.S. Pat. No. 5,763,385; U.S. Pat. No. 5,824,532; U.S. Pat. No. 5,958,739; U.S. Pat. No. 6,008,026, U.S. Pat. No. 6,361,809; U.S. Pat. No. 6,867,031; WO 96/23874; WO 96/39528 and WO 05/001064). Particularly preferred alpha amylases are derived from *Bacillus strains B. stearothermophilus, B. amyloliquefaciens* and *B. licheniformis*. Also reference is made to strains having ATCC 39709; ATCC 11945; ATCC 6598; ATCC 6634; ATCC 8480; ATCC 9945A and NCIB 8059.

Commercially available alpha amylases contemplated for use in the compositions and methods of the invention include; SPEZYME AA; SPEZYME FRED; SPEZYME ETHYL; GZYME G997 (Genencor International Inc.) and TERMAMYL 120-L, LC, SC and SUPRA (Novozymes Biotech).

In addition to the bacterial alpha amylases, fungal alpha amylase are also contemplated for use in the fermentation process of the invention. Suitable fungal alpha amylases are derived from *Aspergillus*, such as *A. oryzae* and *A. niger* (e.g. FUNGAMYL and CLARASE L).

Granular Starch Hydrolyzing Enzymes (GSHEs)—

GSHEs able to hydrolyze granular (raw) starch, and these enzymes have been recovered from fungal, bacterial and plant cells such as *Bacillus* sp., *Penicillium* sp., *Humicola* sp., *Trichoderma* sp. *Aspergillus* sp. *Mucor* sp. and *Rhizopus* sp. In one embodiment, a particular group of enzymes having GSH activity include enzymes having glucoamylase activity and/or alpha amylase activity (See, Tosi et al., (1993) *Can. J. Microbiol.* 39:846-855). A *Rhizopus oryzae* GSHE has been described in Ashikari et al., (1986) *Agric. Biol. Chem.* 50:957-964 and U.S. Pat. No. 4,863,864. A *Humicola grisea* GSHE has been described in Allison et al., (1992) *Curr. Genet.* 21:225-229 and European Patent No. 171218. An *Aspergillus awamori* var. *kawachi* GSHE has been described by Hayashida et al, (1989) *Agric. Biol. Chem* 53:923-929. An *Aspergillus shirousami* GSHE has been described by Shibuya et al., (1990) *Agric. Biol. Chem.* 54:1905-1914.

In one embodiment, a GSHE may have glucoamylase activity and is derived from a strain of *Humicola grisea*, particularly a strain of *Humicola grisea* var. *thermoidea* (see, U.S. Pat. No. 4,618,579). In a preferred embodiment, the *Humicola grisea* var. *thermoidea* is one that has been heterologously expressed in a fungal host cell and particularly in a *Trichoderma* host cell such as a *T. reesei* host cell. In some preferred embodiments, the *Humicola* enzyme having GSH activity will have at least 85%, 90%, 92%, 94%, 95%, 96%, 97%, 98% and 99% sequence identity to the amino acid sequence of SEQ ID NO: 1.

In another embodiment, a GSHE may have glucoamylase activity and is derived from a strain of *Aspergillus awamori*, particularly a strain of *A. awamori* var. *kawachi*. In a preferred embodiment, the *A. awamori* var. *kawachi* is one that has been heterologously expressed in a fungal host cell, such as an *Aspergillus* or *Trichoderma* host cell and particularly a *T. reesei* host cell. In some preferred embodiments, the *A. awamori* var. *kawachi* enzyme having GSH activity will have at least 85%, 90%, 92%, 94%, 95%, 96%, 97%, 98% and 99% sequence identity to the amino acid sequence of SEQ ID NO: 2.

In another embodiment, a GSHE may have glucoamylase activity and is derived from a strain of *Rhizopus*, such as *R. niveus* or *R. oryzae*. The enzyme derived from the Koji strain *R. niveus* is sold under the trade name "CU CONC or the enzyme from *Rhizopus* sold under the trade name GLUZYME.

Another useful GSHE having glucoamylase activity is SPIRIZYME Plus (Novozymes A/S), which also includes acid fungal amylase activity.

In another embodiment, a GSHE may have alpha amylase activity and is derived from a strain of *Aspergillus* such as a strain of *A. awamori, A. niger, A. oryzae*, or *A. kawachi* and particularly a strain of *A. kawachi*.

In a preferred embodiment, the *A. kawachi* is one that has been heterologously expressed in a fungal host cell such as a *Trichoderma* or *Aspergillus* host cell and particularly a *T. reesei* host cell. In some preferred embodiments, the *A. kawachi* enzyme having GSH activity will have at least 85%, 90%, 92%, 94%, 95%, 96%, 97%, 98% and 99% sequence identity to the amino acid sequence of SEQ ID NO: 3.

In some embodiments, the enzyme having GSH activity is a hybrid enzyme, for example one containing a catalytic domain of an alpha amylase such as a catalytic domain of an *Aspergillus niger* alpha amylase, an *Aspergillus oryzae* alpha amylase or an *Aspergillus kawachi* alpha amylase and a starch binding domain of a different fungal alpha amylase or glucoamylase, such as an *Aspergillus kawachi* or a *Humicola grisea* starch binding domain. In other embodiments, the hybrid enzyme having GSH activity may include a catalytic domain of a glucoamylase, such as a catalytic domain of an *Aspergillus* sp., a *Talaromyces* sp., an *Althea* sp., a *Trichoderma* sp. or a *Rhizopus* sp. and a starch binding domain of a different glucoamylase or an alpha amylase. Some hybrid enzymes having GSH activity are disclosed in WO 05/003311, WO 05/045018; Shibuya et al., (1992) *Biosci. Biotech. Biochem* 56: 1674-1675 and Cornett et al., (2003) *Protein Engineering* 16:521-520.

In some embodiments, the amount of GA or a GSHE used in the dry solids staging fermentation process is measured as GAU. In preferred embodiments, one skilled in the art will use the assay as described in the experimental section herein to determine GAU. In addition other methods include the 3,5-dinitrosalicylic acid (DNS) method (See, Goto et al., (1994) Biosci. Biotechnol. Biochem. 58:49-54). In some embodiments, the glucoamylase measured as GAU is between 0.001 to 15.0 GAU/g DS, between 0.01 to 10 GAU/g DS, between 0.01 and 5.0 GAU/g DS; between 0.05 and 10.0 GAU/g DS; between 0.1 and 10.0 GAU/g DS; between 0.1 and 5.0 GAU/g DS; between 0.1 and 2.0 GAU/g DS; and between 0.25 and 1.5 GAU/g DS.

In other embodiments, the amount of an alpha amylase used in the fermentation process is 0.01 to 40 SSU per gram DS, between 0.01 to 30.0 SSU/g DS, between 0.01 to 20 SSU/g DS, between 0.01 to 15.0 SSU/g DS, between 0.01 to 10 SSU/g DS; between 0.01 to 5.0 SSU/g DS; between 0.05 to 10.0 SSU/g DS; between 0.05 to 5.0 SSU g/DS; between 0.1 to 10.0 SSU g/DS; between 0.1 to 5.0 SSU/g DS; between 0.1 to 2.0 SSU/g DS; between 0.25 to 2.5 SSU/g DS; and between 0.5 to 1.5 SSU/g DS.

In some embodiments of the invention, the starch hydrolyzing enzymes are provided in blended compositions. A particularly useful enzymatic composition includes a mixture of an GSHE having alpha amylase activity and a glucoamylase. One useful combination will include a GA having 0.1 to 10 GAU/g DS and an alpha amylase having 0.01 to 15.0 SSU. A particularly useful blend includes a combination of GA from *Aspergillus niger*, such as DISTILLASE and an alpha anylase having GSH activity from *A. kawachi*. Another useful combination includes a GA and the glucoamylase having GSH activity derived from *Humicola grisea*.

In some embodiments, the ratio of a GSHE having alpha amylase activity (SSU) to an enzyme having GA activity (GAU) used in the fermentation will be in the range of 15:1 to 1:15. In further embodiments, the ratio (SSU to GAU) will be in the range of about 10:1 to 1:10; about 10:1 to 1:5; about 5:1 to 1:5; about 4:1 to 1:4; about 3:1 to 1:3; about 2:1 to 1:4 and also about 2:1 to 1:2. In some preferred embodiments, the ratio of SSU to GAU will be between about 4:1 to 2:1.

Secondary Enzymes

Secondary enzymes may be used in the dry solids staging fermentation process according to the invention and some of these include proteases, beta amylases, cellulases, hemicellulases, pullulanases, xylanases, beta-glucanases, phytases, pectinases, xylanases, lipases, cutinases and combinations thereof. Particularly preferred secondary enzymes include proteases, cellulases, pullulanases and beta amylases.

Suitable proteases include microbial proteases, such as fungal and bacterial proteases, for example, acid fungal protease such as FERMENZYME and also GC 106 (Genencor International Inc.). Preferred fungal proteases are derived from strains of *Aspergillus* (e.g. proteases from *A. niger* and *A. oryzae*), *Mucor* (e.g. *M. miehei*), *Trichoderma, Rhizopus*, and *Candida*. Preferred bacterial proteases are derived from strains of *Bacillus* such as *B. amyloliquefaciens*. Proteases added to the fermentation may increase the free amino nitrogen level and increase the rate of metabolism of the yeast and further give higher fermentation efficiency.

Another enzyme that may be used in the methods of the invention include beta-amylases (E.C. 3.2.1.2). These are exo-acting maltogenic amylases, which catalyze the hydrolysis of 1,4-alpha-glucosidic linkages in amylose, amylopectin and related glucose polymers. Commercial beta-amylases are available from Genencor International Inc., and examples include SPEZYME BBA and OPTIMALT BBA.

Cellulases (E.C. 3.2.1.4) such as endo-glucanases may be used in the dry solids staging fermentation process of the invention. Examples of cellulases include cellulases from filamentous fungus such as *Trichoderma, Humicola, Fusarium*, and *Aspergillus*. Commercially cellulases are available as SPEZYME CP (Genencor International, Inc) and CELLUZYME (Novozymes A/S).

Xylanases useful in the dry solids staging fermentation process may be from bacterial or fungal sources, such as *Aspergillus, Trichoderma, Neurospora*, and *Fusarium*. Commercial preparations include SPEZYME CP (Genencor International, Inc.) and ULTRAFLOW (Novozymes A/S).

Examples of phytases such as (E.C. 3.1.3.8 and 3.1.3.26) include PHYTASE (Novozymes A/S).

The effective amount of these enzymes to be included in the dry solids staging fermentation process can be readily determined by one skilled in the art.

Fermenting Organisms

Depending on the desired end-product, different fermenting organisms may be used in the dry solids staging fermentation process. These fermenting organisms may be wild-type organisms or modified organisms. For example, modified organisms that heterologously express an enzyme or over express enzymes that are normally produced by the wild-type organism. Preferred examples of fermenting organisms are ethanologenic microorganisms or ethanol producing microorganisms such as ethanologenic bacteria which express alcohol dehydrogenase and pyruvate dehydrogenase and which can be obtained from *Zymomonas moblis* (See e.g. U.S. Pat. No. 5,000,000; U.S. Pat. No. 5,028,539, U.S. Pat. No. 5,424, 202; U.S. Pat. No. 5,514,583 and U.S. Pat. No. 5,554,520). In additional embodiments, the ethanologenic microorganisms express xylose reductase and xylitol dehydrogenase, enzymes that convert xylose to xylulose. In further embodiments, xylose isomerase is used to convert xylose to xylulose. In particularly preferred embodiments, a microorganism capable of fermenting both pentoses and hexoses to ethanol are utilized. For example, in some embodiments the microorganism may be a natural or non-genetically engineered microorganism or in other embodiments the microorganism may be a recombinant microorganism. For example, in some embodiments the preferred fermenting microorganisms include bacterial strains from *Bacillus, Lactobacillus, E. coli, Erwinia, Pantoea* (e.g., *P. citrea*) and *Klebsiella* (e.g. *K. oxytoca*). (See e.g. U.S. Pat. No. 5,028,539, U.S. Pat. No. 5,424, 202 and WO 95/13362).

In further preferred embodiments, the ethanol producing microorganism is a fungal microorganism, such as a yeast and specifically *Saccharomyces* such as strains of *S. cerevisiae* (U.S. Pat. No. 4,316,956). A variety of *S. cerevisiae* are commercially available and these include FALI (Fleischmann's Yeast), SUPERSTART (Alltech), FERMIOL (DSM Specialties), RED STAR (Lesaffre) and Angel alcohol yeast (Angel Yeast Company, China).

In some embodiments, in addition to the raw materials described above, fermentation media will contain supplements including but not limited to vitamins (e.g. biotin, folic acid, nicotinic acid, riboflavin), cofactors, and macro and micro-nutrients and salts (e.g. $(NH4)_2SO_4$; $K_2HPO_4$; NaCl; $MgSO_4$; $H_3BO_3$; $ZnCl_2$; $CaCl_2$).

Process:

Although there may be various superficial resemblances between the dry solids staging fermentation process of the instant invention and methods known in the art, the present invention provides more comprehensive objectives that are reflected in a number of detail features believed to be unique to the practice of this invention. In some embodiments, these features notably include: directly feeding a solid fermentable substrate into the fermentation vessel, starting the initial fermentation step with a low initial DS which is less than the accumulated DS and may even be 0%, adding dry solids in the loading step after the fermentation is proceeding, controlling the fermentation by feeding solids during the loading step, and enhancing the fermentation efficiency by adding fermentable substrates during the logarithmic growth phase of the fermenting organism.

The main process steps of the dry solids staging fermentation process encompassed herein may in one embodiment be described as separated into the following steps: the initial fermentation step and the loading step.

Initial Fermentation Step:

In some embodiments of the initial fermentation step, the fermentable substrate is combined with one or more starch hydrolyzing enzymes and a fermenting organism in a fermentation vessel to start the initial fermentation.

While the fermentable substrate may be any substrate as disclosed under the raw materials description, in some embodiments the fermentable substrate is a solid fermentable substrate and particularly a dry ground cereal grain which has been milled to a fine particle size (for example wherein at least 90% of the grain passes through a 0.5 mm mesh sieve and in other embodiments the dry cereal grain has been milled to a coarse particle size or not milled at all.

In some preferred embodiments, the fermentable substrate is a grain which has been either wet milled or dried milled and optionally fractionated. In other preferred embodiments, the fermentable substrate is a fermentable sugar.

In some embodiments, the fermentable substrate may be pretreated prior to the dry solids staging fermentation process. The pretreatment may include any one or a combination of the following, presoaking, dilute acid treatment, alkaline treatment and enzymatic treatment. In some embodiments, the pretreatment may be conducted for 30 minutes to 24 hours, also from 30 minutes to 12 hours, also from 30 minutes to 8 hours, also from 30 minutes to 4 hours and preferably from 1 hour to less than 3 hours.

In some conventional processes, when the fermentable substrate is a grain or other plant based substrate which includes granular starch, the substrate is milled, mixed with an aqueous liquid and held in a slurry or holding tank. The slurry comprising the substrate that includes granular starch is mixed or agitated to prevent settling and clogging of the slurry tank due to the viscosity of the solids in the slurry. The slurry from the tank is then feed into a saccharification tank. These slurry tanks potentially provide an environment for promoting microbial contamination.

Figure 1C:
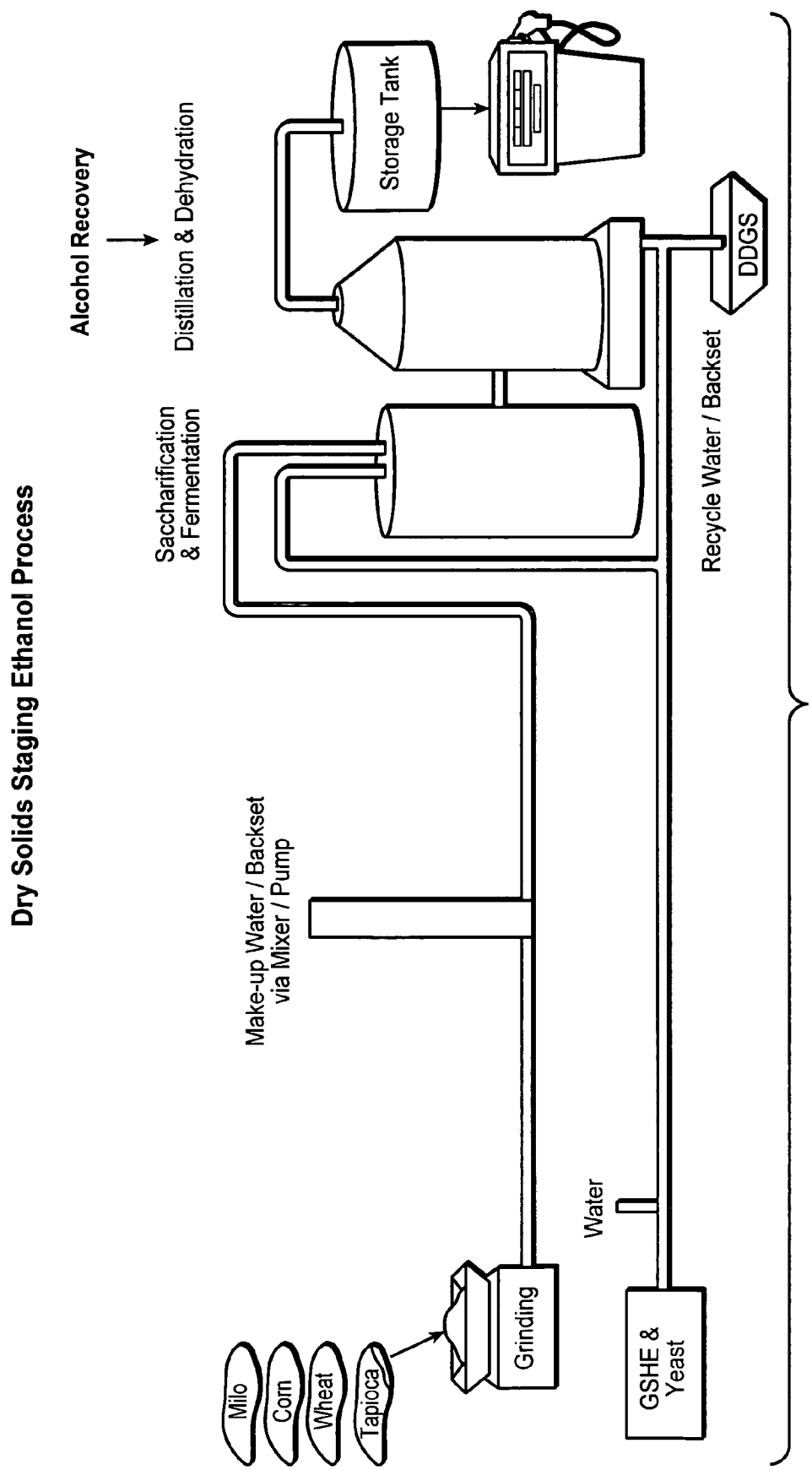
FIG. 1C illustrates an embodiment of the dry solids staging fermentation process encompassed by the instant invention, which includes the direct feeding of a dry ground cereal grain during the initial fermentation step and the loading step into a saccharification and fermentation vessel with the elimination of a slurry tank comprising an aqueous mixture of the cereal grain comprising granular starch.

In one embodiment of the dry solids staging fermentation process encompassed by the invention, the combining of a solid fermentable substrate with an aqueous liquid in a slurry or holding tank or the like is eliminated because the solid fermentable substrate is directly fed into the saccharification/fermentation (S/F) vessel. Water or other aqueous liquid may be combined with the solid fermentable substrate prior to addition of the substrate into the S/F vessel, but this addition is accomplished by an in-line feed means, such as by directly adding aqueous liquid to the solid fermentable feed transfer conduit such as a pipe which feeds the fermentable substrate into the S/F vessel or by feeding the solid fermentable substrate to a pump which mixes the substrate with an aqueous liquid and feeding the slurry into the S/F vessel. The addition of the aqueous liquid by an in-line feed means may be accomplished at any point during the transfer of the solid fermentable substrate to the S/F vessel. In some embodiments, the aqueous liquid will be water and in other embodiments of the process the aqueous liquid will be thin-stillage (FIG. 1C). Recycled thin-stillage, which can be added in the fermentation process is sometimes referred to in the art as backset.

During the initial fermentation step the combining of the fermentable substrate with one or more starch hydrolyzing enzymes and fermenting organisms may be accomplished in a number of ways that one skilled in the art would readily be able to determine. In some embodiments, the addition of all ingredients (raw materials) to the fermentation vessel is essentially contemporaneous. In other embodiments, aqueous liquid, one or more starch hydrolyzing enzymes and the yeast are combined in the fermentation vessel and the fermentable substrate and particularly a solid fermentable substrate is subsequently added. In yet other embodiments, the fermentable substrate is combined with the aqueous liquid in the fermentation vessel first and then starch hydrolyzing enzymes and yeast are added to the vessel. While the preferred embodiment of the dry solids staging fermentation process is a simultaneous saccharification and fermentation process, in other embodiments the dry solids staging fermentation process may include separate saccharification and fermentation vessels.

In preferred embodiments there are no further additions of the one or more starch hydrolyzing enzymes or fermenting organisms during the initial fermentation step.

In some embodiments, the initial fermentation is conducted at a temperature of at least about 5° C., 10° C., 15° C., 20° C., 25° C., 30° C., 35° C., 40° C., 45° C., 50° C., 55° C., 60° C., 65° C., 70° C., and 75° C. and also at a temperature of less than 70° C., less than 65° C. and less than 60° C. In other embodiments, the temperature will be between about 5-65° C., about 10-65° C., about 20-65° C., about 20-60° C., about 20-55° C., about 25-50° C., about 25-45° C., about 30-45° C., about 30-40° C. and about 35-45° C. In all embodiments, the temperature of the initial fermentation will be below the gelatinization temperature of the granular starch in the fermentable substrate.

In some embodiments, the initial fermentation is conducted at a pH of between pH 3.0 and 7.0, between pH 3.0 and 6.5, between pH 3.0 and 6.0, between pH 3.0 and 5.0, between pH 3.5 and 5.5, between pH 3.5 to 5.0, and between pH 3.5 and 4.5. The exact temperature and pH used in accordance with any of the fermentation steps of the instant process depends upon the specific fermentable substrate and further may depend upon the particular plant variety, enzymes that are being used and the fermenting organism.

A fermenting organism goes through different stages of growth including a lag phase, logarithmic phase, a stationary phase and a death phase. The length of the lag phase may vary depending on nutrition, growth conditions, temperature, and inoculation density. Also the lag phase may depend on whether or not the fermenting organism, such as yeast were acclimatized or directly added to a fermenter. Generally the lag phase is 6 to 9 hours. If a fermenting organism such as yeast can be kept in an active growth state, production of end products such as alcohol and particularly ethanol could be increased and fermentation time potentially decreased.

Therefore, in some embodiments the initial fermentation is conducted for a period of time that corresponds to the lag phase of the fermenting organism. In other embodiments, the initial fermentation step is conducted for a period of time between 2 to 40 hours, also between 2 to 30 hours, also between 2 to 25 hours, also between 5 and 20 and between 2 and 15 hours. In some embodiments, the initial fermentation time is greater than 2, 3, 4, 5, 6, 7, 8, 9, 10 or 15 hours but less than 36 hours.

In some embodiments, the % DS of the slurry comprising the fermentable substrate in the initial fermentation step (initial DS) will be between 0 to 45%, between 0 to 40%, between 2 to 30%, between 5 to 25% and also in some embodiments between 5 to 20%. In some embodiments, and particularly wherein the fermentable substrate is a solid fermentable substrate, such as a dry cereal grain, the DS of the mash of the initial fermentation is at least 2%, 5%, 6%, 7%, 8%, 9%, 10%, 12%, 15%, 20%, 22% and 25%. In some embodiments, the DS of the mash is less than 40%, less than 30%, less than 28%, less than 26%, less than 25% and less than 24%. In other embodiments, the DS is between 1 and 25%.

While any number of the starch hydrolyzing enzymes as described in the raw material section may be used in the dry solids staging fermentation process, in preferred embodiments the starch hydrolyzing enzymes are glucoamylases, alpha amylases, granular starch hydrolyzing enzymes or a combination thereof. Particularly preferred enzyme compositions include a combination of glucoamylases and an enzyme having granular starch hydrolyzing activity. For example, an *Aspergillus niger* glucoamylase and an *Aspergillus kawachi* alpha amylase may be used.

Loading Step:

In preferred embodiments of the dry solids staging fermentation process, further additions of the fermentable substrate are added in a loading step to the same fermentation vessel as the initial fermentation step. In some embodiments, the fermentable substrate is the same as the fermentable substrate added in the initial fermentation step, and in other embodiments, the fermentable substrate is a different fermentable substrate.

Similar to the initial fermentation step, in some embodiments the solid fermentable substrate may be a grain which has been milled to a fine particle size (for example wherein at least 90% of the grain passes through a 0.5 mm mesh sieve and in other embodiments the dry cereal grain has been milled to a coarse particle size or not milled at all.

In some embodiments, the fermentable substrate of the initial fermentation step is a soluble sugar, such as molasses or glucose syrup and the fermentable substrate of the loading step is a solid fermentable substrate such as a milled or non-milled cereal grain or fractionated part thereof. When the fermentable substrate of the initial fermentation step is a soluble sugar and the fermentable substrate of the loading step is a solid fermentable substrate, such as a dry cereal grain, an enzyme having granular starch hydrolyzing activity will be included in the fermentation tank with the solid fermentable substrate. In some embodiments, different fermentable substrates may be added to the fermentation vessel during the loading step.

The solid fermentable substrate may be directly fed into the S/F vessel during the loading step in the same manner as described for the initial fermentation step. In some embodiments the direct feeding will be accomplished by an in-line feed means.

During the loading step, the feeding of the fermentable substrate may be a continuous feed, an interval feed or a one time bulk feed which is essentially at the beginning of the loading step. Intervals may comprise minutes or hours. In some embodiments, the feeding intervals may be every 5, 10, 15, 20 or 30 minutes. The feeding may also be carried out at hourly intervals, for example every 1, 2, 3, 4, 5, or 10 hours. In some embodiments, the feeding during the loading step will continue for a period of time of between about 5 to 35 hours, also about 5 to 25 hours and 5 to 20 hours. In some embodiments, the feeding during the loading step may continue for 1, 2, 3, 4, 5, 6, 7, 8, 9, 10, 15, 20, 25 or 30 hours or more. The feeding may continue for various periods of time and this may depend a number of factors including the fermentable substrate. In some embodiments, the feeding of the fermentable substrate will be at a rate equal to or different from the rate of conversion of the fermentable substrate to the end product.

In some embodiments, the initial fermentation will be conducted from 5 to 36 hours and the feeding of the loading step will be conducted from 10 to 20 hours. The addition of the second fermentable substrate may be made during the logarithmic phase of the fermenting organism (active growth phase).

The % DS of the fermentation broth will increase over time such that in some embodiments the accumulated DS will be between about 10 to 55%. In other embodiments, the accumulated DS will be between about 10 to 50%, about 15 to 45%, about 20 to 40%, about 25 to 40% and about 10 to 20%.

In some embodiments, while the accumulated DS added to the fermentation broth will be between about 10 and 55%, the DS of the initial fermentation medium will be at least 5%, at least 10%, least 15% less, at least 20%, at least 25% less, at least 30% less, at least 40% less, at least 50% less, at least 60% less, at least 70% less, at least 80% less, and at least 90% less than the DS of the accumulated DS of the fermentation broth. One skilled in the art will be readily able to calculate the amount of fermentable substrate to be added during the dry solids staging fermentation process to obtain a DS of a given %.

In other embodiments, when approximately 50%, 60%, 70%, 80% 90% of the DS is converted to soluble solids, another feeding of the fermentable substrate will take place in the loading step.

While it is contemplated that in some embodiments the loading step will not require additional inoculums of fermenting organisms or additional starch hydrolyzing enzymes, certain embodiments will comprise the addition of inoculums such as yeast and/or starch hydrolyzing enzymes. Further in some embodiments, additional yeast inoculums may be added, for example at between 5 to 40 hours, between 10 to 40 hours, between 12 to 30 hours or between 15 and 24 hours after initiation of the loading step.

The loading step may be conducted at a temperature and pH as described above for the initial fermentation step. In some embodiments, the temperature and pH will be essentially the same as the temperature and pH of the initial fermentation step and in other embodiments the temperature and pH may vary from the initial fermentation step. For example, in some embodiments, the temperature of the initial fermentation step may be between 25° C. to 40° C. or between 30° C. to 50° C. and the temperature of the loading step may be decreased in increments of 1° C., 2° C., 3° C., 4° C., 5° C., 6° C., 7° C., 8° C., 9° C. or 10° C. In some embodiments, the temperature of the initial fermentation step will be between 35° C. to 40° C. and the temperature of the loading step will be between 25° C. to 35° C.

The general starch gelatinization temperature ranges for a number of starches in fermentable substrates which may be used in accordance with the dry solids staging fermentation process includes barley (52 to 59° C.), wheat (58 to 64° C.), rye (57 to 70° C.), corn (62 to 72° C.), high amylose corn (67 to 80° C.), rice (68 to 77° C.), sorghum (68 to 77° C.), potato (58 to 68° C.), tapioca (59 to 69° C.) and sweet potato (58 to 72° C.). (J. J. M. Swinkels pg 32-38 in STARCH CONVERSION TECHNOLOGY, Eds Van Beynum et al., (1985) Marcel Dekker Inc. New York and The Alcohol Textbook $3^{rd}$ ED. A reference for the beverage, fuel and industrial alcohol industries, Eds Jacques et al., (1999) Nottingham University Press, UK). In accordance with the invention herein the fermentations will be conducted at a temperature below the starch gelatinization temperature of the starch contained in the fermentable substrate.

In some embodiments the total fermentation time of the dry solids staging process will be for about 24 to 168 hours, 24 to 144 hours, 24 to 108 hours; 24 to 96 hours, 36 to 96 hours, 36 to 72 hours and 48 to 72 hours.

The yield of glucose (percent of the total solubilized dry solids) from a fermentable substrate in the dry solids staging process may be at least about 60%, 65%, 70%, 75%, 80%, 85%, 90%, 91%, 92%, 93%, 94%, 95%, 96%, 97% and 98%. However, in a preferred embodiment, the glucose is continually produced and substantially all of the glucose is used in the process to produce an end-product, such as ethanol. In further embodiments, the final mash from the dry solids staging fermentation process will include less than 1.0%, less than 0.8%, less than 0.5%, less than 0.2%, less than 0.15%, less than 0.1%, and less than 0.05% DP-1 (w/v).

While the preferred end-product is an alcohol and particularly ethanol, other end-products may be obtained and these include without limitation, glycerol, ASA intermediates, 1,3-propanediol, enzymes, antimicrobials, organic acids, amino acids and antibiotics.

In some embodiments, the yield of ethanol will be greater than 8%, 10%, 12%, 14%, 16%, 18% and 20% by volume. In other embodiments, at least 50%, 60%, 70%, 80% of the final ethanol yield is produced in the first 20, 22, 24, 26, 28 or 30 hours. In certain embodiments, the yield of ethanol will be greater than 16% and at least 50% of the final ethanol will be produced in the first 20 hours. The ethanol obtained according to the dry solids staging fermentation process may be used as a fuel ethanol, potable ethanol or industrial ethanol.

The mash at the end of the dry solids staging fermentation may include from 0 to 30% residual starch. In some embodiments, the mash may include at least 1%, 2%, 4%, 6%, 8%, 10%, 12% but less than 30%, less than 20% and less than 15% residual starch.

In some embodiments, the dry solids staging fermentation process will have a higher carbon conversion efficiency when compared with other no-cook or low temperature fermentation processes under essentially the same fermentation conditions of for example, fermentable substrate, pH, temperature, time of fermentation and the like. The carbon conversion efficiency may be defined as an increase in the conversion of carbon in the fermentable substrate directly into an end-product, such as alcohol without loosing carbon as a by-product. In some embodiments, the increase in carbon conversion efficiency when the dry solids staging fermentation process is used compared to a non-cook fermentation process using the same raw material under essentially the same conditions will be at least 2%, at least 5%, at least 7%, at least 10%, at least 15% and at least 20%. In some embodiments, the increased carbon conversion efficiency is reflected in the higher residual starch levels at the end of a fermentation, which yields approximately the same amount of ethanol as the process to which it is being compared. In some preferred embodiments, the fermentable substrate will be a grain, such as corn, wheat, barley or rye.

In further embodiments, the end-product produced according to the method will be separated and/or purified from the fermentation media. Methods for separation and purification are known, for example by subjecting the media to extraction, distillation and column chromatography. In some embodiments, the end product is identified directly by submitting the media to high-pressure liquid chromatography (HPLC) analysis.

In further embodiments, the mash may be separated by for example centrifugation into the liquid phase and solids phase and end-products such as alcohol and solids recovered. The alcohol may be recovered by means such as distillation and molecular sieve dehydration or ultra filtration.

The remaining residue of the fermentation, known as stillage may also be recovered and components of the stillage recycled for use in the loading step or the stillage may be separated into a soluble fraction or insoluble fraction.

When the stillage is separated for example by centrifugation or screening into a soluble fraction and an insoluble fraction, these fractions can be used to make distillers' solubles or distillers' dried solubles or mixed together to make distillers' dried grain plus solubles (DDGS). One skilled in the art is familiar with processes for forming DDGS and distillers' grains in general. The DDGS may then be used for example, in an animal feed formulation.

In some embodiments, the dry solids staging process will result in a DDGS containing less than 30%, less than 20%, less than 15%, less than 10%, less than 9%, less than 8%, less than 7%, less than 6%, less than 5%, less than 4%, less than 2% and less than 1% residual starch. In some embodiments, the DDGS which results from the process according to the invention will have higher residual starch content and in other embodiments will have lower residual starch content compared to DDGS prepared by prior art processes. The DDGS obtained from the dry solids staging process may be used in animal feeds. In addition, the residual starch, which is recovered from the fermentation may be used as a fermentable substrate.

Various other examples and modification of the description and examples will be apparent to a person skilled in the art after reading the disclosure without departing from the spirit and scope of the invention, it is intends that all such examples or modification be included within the scope of the appended claims.

EXPERIMENTAL

The following examples are provided in order to demonstrate and further illustrate certain preferred embodiments and aspects of the present invention and are not to be construed as limiting the scope thereof. Indeed, it is contemplated that these teachings will find use in further optimizing the process systems described herein.

In the disclosure and experimental section which follows, the following abbreviations apply: GA (glucoamylase); AkAA (*Aspergillus kawachi* alpha amylase having GSH activity; SEQ ID NO: 3); AnGA/AkAA (an enzyme blend having GSH activity which includes *Aspergillus niger* glucoamylase and *Aspergillus kawachi* alpha amylase); wt % (weight percent); ° C. (degrees Centigrade); rpm (revolutions per minute); $H_2O$ (water); $dH_2O$ (deionized water); $diH_2O$ (deionized water, Milli-Q filtration); aa (amino acid); bp (base pair); kb (kilobase pair); kD (kilodaltons); g or gm (grams); μg (micrograms); mg (milligrams); μL (microliters); ml and mL (milliliters); mm (millimeters); μm (micrometer); M (molar); mM (millimolar); μM (micromolar); U (units); V (volts); MW (molecular weight); sec (seconds); min(s) (minute/minutes); hr(s) (hour/hours); DO (dissolved oxygen); phthalate buffer (sodium phthalate in water, 20 mM, pH 5.0); w/v (weight to volume); w/w (weight to weight); v/v (volume to volume); Genencor (Genencor International, Inc., Palo Alto, Calif.); DDGS (Distilleries Dry Grain plus Solids); MT (Metric ton); and EtOH (ethanol).

The following assays and methods are used in the examples provided below:

Glucoamylase activity was measured using a well-known assay which is based on the ability of glucoamylase to catalyze the hydrolysis of p-nitrophenyl-alpha-D-glucopyranoside (PNPG) to glucose and p-nitrophenol. At an alkaline pH, the nitrophenol; forms a yellow color that is proportional to glucoamylase activity and is monitored at 400 nm and compared against an enzyme standard measured as a GAU.

One "Glucoamylase Activity Unit" (GAU) is defined as the amount of enzyme that will produce 1 gm of reducing sugar, calculated as glucose per hour from a soluble starch substrate (4% DS) at pH 4.2 and 60° C.

The measurement of alpha amylase activity is based on the degree of hydrolysis of soluble potato starch substrate (4% DS) by an aliquot of the enzyme sample at pH 4.5, 50° C. The reducing sugar content is measured using the DNS method as described in Miller, G. L. (1959) *Anal. Chem.* 31:426-428. One unit of the enzyme activity (SSU, soluble starch unit) is equivalent to the reducing power of 1 mg of glucose released per minute at the specific incubation conditions.

Determination of Total Starch Content:

The enzyme-enzyme starch liquefaction and saccharification process was used to determine the total starch content. In a typical analysis, 2 g of the dry sample was taken in a 100 ml Kohlraucsh flask and 45 ml of MOPS buffer, pH 7.0 was added. The slurry was well stirred for 30 min. SPEZYME FRED (1:50 diluted in water), 1.0 ml was added and heated to boiling for 3-5 min. The flask was placed in an autoclave maintained at 121° C. for 15 min. After autoclaving the flask was placed in a water bath at 95° C. and 1 ml of 1:50 dilutes SPEZYME FRED was added and incubated for 45 min. The pH was adjusted to pH 4.2 and the temperature was reduced to 60° C. This was followed by addition of 20 ml acetate buffer, pH 4.2. Saccharification was carried out by adding 1.0 ml of 1:100 diluted OPTIDEX L-400 (Glucoamylase from Genencor International Inc.) and the incubation was continued for 18 hr at 60° C. The enzyme reaction was terminated by heating at 95° C. for 10 min. The total sugar composition was determined by HPLC analysis using glucose as a standard. The soluble starch hydrolysate from water extraction of a sample at room temperature without enzymatic treatment was subtracted from the total sugar.

Residual Starch Iodine Test:

A sample of the beer (fermentation broth) was centrifuged in 2 ml plastic centrifuge tubes. The supernatant was decanted and the tube containing the pellet was placed in an ice bath. Several drops of 0.025N iodine solution (0.1N iodine from VWR Cat. No. VW3207-1 diluted 4×) was added to the pellet and mixed. A positive (+) starch shows a range of color from blue to purple and the intensity of color is directly proportional to the concentration of starch. A negative result (−) remains yellowish.

Total Protein Analysis:

The total nitrogen (N) in the sample preparations was determined using the Kjeldhal method (American Assoc. Cereal Chemists (AACC), (1983), Methods 22B60 8th Ed. St Paul, Minn.). Protein content was calculated by 6.25×total N.

Ethanol and Carbohydrate Determinations:

Ethanol and carbohydrate composition of the samples were determined using the HPLC method as described herein:

a) a 1.5 mL Eppendorf centrifuge tube was filled with fermentor beer and cooled on ice for 10 min;

b) the sample tube was centrifuged for 1 min in Eppendorf table top centrifuge;

c) a 0.5 mL sample of the supernatant was transferred to a test tube containing 0.05 mL of Kill solution (1.1N $H_2SO_4$) and allowed to stand for 5 min;

d) 5.0 mL of water is added to the test tube sample and then filtered into a HPLC vial through 0.45 μm Nylon Syringe Filter; and e) run on HPLC.

HPLC Conditions:

a) Ethanol System: Column: Phenomenex Rezex Organic Acid Column (RHM-Monosaccharide) #00H 0132-KO (Equivalent to Bio-Rad 87H); Column Temperature: 60° C.; Mobile Phase: 0.01 N $H_2SO_4$; Flow Rate: 0.6 mL/min; Detector: RI; and Injection Volume: 20 μL.

b) Carbohydrate System: Column: Phenomenex Rezex Carbohydrate (RCM-Monosaccharide) #00H-0130-KO (Equivalent to Bio-Rad 87H); Column Temperature: 70° C.; Mobile Phase: Nanopure DI $H_2O$; Flow Rate: 0.8 mL/min; Detector: RI; Injection Volume: 10 μL (3% DS material)

The column separates based on the molecular weight of the saccharides, which are designated as DP1 (monosaccharides); DP2 (disaccharides); DP3 (trisaccharides) and DP greater than 3 (oligosaccharide sugars having a degree of polymerization greater than 3).

Example 1

Batch Fermentation

Five hundred (500) g of finely ground corn (having 14% moisture, a particle size wherein 100% passed through a 40 mesh sieve which is equivalent to 0.420 mm (ASTM), 30% deoiled germ with a starch content of 40%, total starch content of 67%, CR Ethanol, Zhaodong, Heilongjiang, China) was added to a 2-liter bioreactor containing 1.0 liter of distilled water and equipped with a temperature and pH control programming system. Dry urea was added at 1000 ppm. The pH was adjusted to pH 4.5 using dilute sulphuric acid. After uniform mixing and temperature stabilization (30° C.), AnGA/AkAA was added at 0.75 GAU/g DS and followed by the addition of dry yeast (0.8% Fali Yeast, Ah Cheng, Heilongjiang, China), and urea (0.1%, Wuxi Minfeng, Wuxi, China). The fermentation medium was continuously stirred to avoid the settling of the ground corn. Samples of fermentation broth were taken at different time intervals and centrifuged. The composition of reaction products was determined by HPLC analysis. To determine fermentation efficiency, the residual starch of the fermentation broth was analyzed at 72 hrs.

TABLE 1

Reaction products from fermentation of ground corn (30% DS) at 30° C., pH 4.5

| Time (hrs) | DP > 3 % w/v | DP-3 % w/v | DP-2 % w/v | DP-1 % w/v | Succinic Acid % w/v | Lactic Acid % w/v | Glycerol % w/v | Acetic Acid % w/v | Ethanol % v/v |
|---|---|---|---|---|---|---|---|---|---|
| 24 | 0.46 | 0.00 | 0.03 | 0.08 | 0.14 | 0.12 | 0.87 | 0.05 | 10.73 |
| 47 | 0.30 | 0.00 | 0.05 | 0.04 | 0.18 | 0.13 | 1.05 | 0.07 | 15.13 |
| 72 | 0.34 | 0.04 | 0.07 | 0.00 | 0.21 | 0.09 | 1.09 | 0.07 | 16.34 |

The ethanol concentration in the fermentation broth increased with fermentation time to reach 16.34% v/v at 72 hours. The residual starch contend of the fermentation broth at 72 hours was 10.71%.

Example 2

Dry Solids Staging Process with Loading of Dry Ground Corn

The fermentation was carried out as described above with the following differences. The bioreactor was initially charged with ground corn at 15% DS (half of the accumulated DS of the fermentation), AnGA/AkAA at 0.75 GAU/g based on a final 30% DS. The fermentation was conducted at 30° C. Starting at approximately 22 hours after commencing initial fermentation, dry ground corn (15.4 g) was added at hourly intervals for 16 hours (total fermentation time=38 hours). Fermentation was continued until 72 hours. The composition of reaction products of the supernatant was analyzed by HPLC and residual starch was determined at 72 hours.

TABLE 2

Reaction products from fermentation with loading of dry ground corn

| Time hrs | DP > 3 % w/v | DP-3 % w/v | DP-2 % w/v | DP-1 % w/v | Succinic Acid % w/v | Lactic Acid % w/v | Glycerol % w/v | Acetic Acid % w/v | Ethanol % v/v |
|---|---|---|---|---|---|---|---|---|---|
| 6 | 0.26 | 0.03 | 0.05 | 0.36 | 0.07 | 0.05 | 0.87 | 0.06 | 2.69 |
| 21 | 0.20 | 0.03 | 0.02 | 0.05 | 0.11 | 0.09 | 0.79 | 0.05 | 7.94 |
| 25 | 0.22 | 0.04 | 0.02 | 0.03 | 0.12 | 0.09 | 0.77 | 0.00 | 9.18 |
| 30 | 0.36 | 0.04 | 0.02 | 0.04 | 0.11 | 0.08 | 0.85 | 0.00 | 10.40 |
| 38 | 0.53 | 0.09 | 0.19 | 0.13 | 0.18 | 0.16 | 0.93 | 0.10 | 11.98 |

TABLE 2-continued

Reaction products from fermentation with loading of dry ground corn

| Time hrs | DP > 3 % w/v | DP-3 % w/v | DP-2 % w/v | DP-1 % w/v | Succinic Acid % w/v | Lactic Acid % w/v | Glycerol % w/v | Acetic Acid % w/v | Ethanol % v/v |
|---|---|---|---|---|---|---|---|---|---|
| 46 | 0.44 | 0.05 | 0.02 | 0.15 | 0.17 | 0.13 | 1.05 | 0.08 | 14.17 |
| 72 | 0.28 | 0.05 | 0.04 | 0.00 | 0.19 | 0.13 | 1.50 | 0.09 | 17.16 |

Similar to example 1, the ethanol content was increased with an increase in fermentation time. By 72 hours the ethanol content was 17.15% (v/v), which was higher than in example 1. The residual starch content of the fermentation broth at 72 hours was 11.1%.

Comparison of the results from Table 1 and 2 demonstrate an improvement in the carbon conversion efficiency using the dry corn feeding of example 2. This conclusion is supported by the higher % ethanol obtained at 72 hours from the dry ground corn feeding (17.16% vs. 16.34%) in spite of the higher residual starch (11.1% vs. 10.17%).

Example 3

Dry Ground Cereal Grain Feeding During the Loading Step and Effect of Initial DS Fermentations were carried out as described above in example 1, but with different starting DS. Degermed ground corn from CR Ethanol, Zhaodong, Heilongjiang, China was used which passed 100% thru a 40-mesh screen. In a 2-liter biorector, 816 to 830 grams of the ground corn based on the moisture content, (measured using a Sartorius AG Gottingen MA 30-00V3), and 1400 or 1500 grams of tap water were mixed and 0.1% of urea based on the DS was added. The pH of the slurry was adjusted to pH 4.7 using 26% sulphuric acid. AnGA/AkAA was added at 1.0 GAU/g DS based on a final DS of 30%. The bioreactor was inoculated with 0.8% DS dry Angel yeast (Hubei Angel Yeast Co. Ltd, China). The fermentation medium was mixed at slow agitation at 30° C. The initial DS was adjusted to 7, 10 and 15%. The AnGA/AkAA was added based on a final 30% DS. Starting at 15 hours, dry solid ground corn was added directly to the fermenter at one hour intervals for 10 hours in equal amounts. The weight of the dry solid corn addition was adjusted to reach a final DS of 30%. The pH of the fermentation was maintained at pH 4.7. Samples were taken at 15, 24, 48 and 72 hours and analyzed by HPLC. The residual starch content was determined from the fermenter broth sample at 72 hours.

TABLE 3A

Ethanol Production with total 30% DS dry corn substrate addition at 0 hr

| Sampled (hr) | DP > 2 % w/v | DP-2 % w/v | DP-1 % w/v | Lactic Acid % w/v | Glycerol % w/v | Ethanol % v/v |
|---|---|---|---|---|---|---|
| 7 | 0.35 | 0.11 | 1.00 | 0.10 | 0.68 | 4.69 |
| 24 | 0.25 | 0.04 | 1.20 | 0.10 | 0.97 | 11.66 |
| 30 | 0.13 | 0.04 | 1.34 | 0.11 | 0.98 | 13.38 |
| 48 | 0.05 | 0.12 | 0.44 | 0.12 | 1.07 | 16.42 |
| 54 | 0.03 | 0.10 | 0.25 | 0.12 | 1.13 | 17.22 |
| 72 | 0.23 | 0.07 | 0.34 | 0.11 | 1.21 | 17.06 |

TABLE 3B

Ethanol production with an initial 7% DS and accumulated 30% DS, dry corn substrate feeding at 15 to 25 hr feed time

| Sampled (hr) | DP > 2 % w/v | DP-2 % w/v | DP-1 % w/v | Lactic Acid % w/v | Glycerol % w/v | Ethanol % v/v |
|---|---|---|---|---|---|---|
| 15 | 0.08 | 0.00 | 0.02 | 0.05 | 0.49 | 4.62 |
| 24 | 0.31 | 0.05 | 0.40 | 0.11 | 0.82 | 8.58 |
| 40 | 0.23 | 0.04 | 1.05 | 0.13 | 1.13 | 13.98 |
| 48 | 0.31 | 0.04 | 0.92 | 0.14 | 1.24 | 15.57 |
| 64 | 0.14 | 0.02 | 0.09 | 0.12 | 1.34 | 17.71 |
| 68 | 0.14 | 0.01 | 0.05 | 0.11 | 1.25 | 17.78 |
| 72 | 0.13 | 0.01 | 0.04 | 0.12 | 1.55 | 17.57 |

TABLE 3C

Ethanol production with initial 10% DS and accumulated 30% DS, dry corn substrate feeding at 15 to 25 hr feed time

| Sampled (hr) | DP > 2 % w/v | DP-2 % w/v | DP-1 % w/v | Lactic Acid % w/v | Glycerol % w/v | Ethanol % v/v |
|---|---|---|---|---|---|---|
| 15 | 0.16 | 0.01 | 0.03 | 0.04 | 0.52 | 5.73 |
| 25 | 0.44 | 0.04 | 0.16 | 0.11 | 0.93 | 9.58 |
| 40 | 0.39 | 0.04 | 0.35 | 0.12 | 1.22 | 14.16 |
| 48 | 0.39 | 0.03 | 0.12 | 0.13 | 1.14 | 15.72 |
| 64 | 0.49 | 0.04 | 0.00 | 0.14 | 1.15 | 17.31 |
| 72 | 0.32 | 0.05 | 0.00 | 0.14 | 1.14 | 18.11 |

TABLE 3D

Ethanol production with initial 15% DS and accumulated 30% DS, dry corn substrate feeding at 15 to 25 hrs

| Sampled (hr) | DP > 2 % w/v | DP-2 % w/v | DP-1 % w/v | Lactic Acid % w/v | Glycerol % w/v | Ethanol % v/v |
|---|---|---|---|---|---|---|
| 15 | 0.13 | 0.03 | 0.17 | 0.09 | 0.72 | 7.68 |
| 25 | 0.28 | 0.04 | 0.49 | 0.11 | 0.94 | 10.97 |
| 40 | 0.28 | 0.04 | 1.25 | 0.12 | 1.01 | 14.19 |
| 48 | 0.31 | 0.06 | 1.04 | 0.12 | 1.12 | 16.01 |
| 64 | 0.35 | 0.07 | 0.35 | 0.11 | 1.19 | 17.17 |
| 72 | 0.35 | 0.11 | 0.47 | 0.12 | 1.27 | 18.50 |

Figure 2:
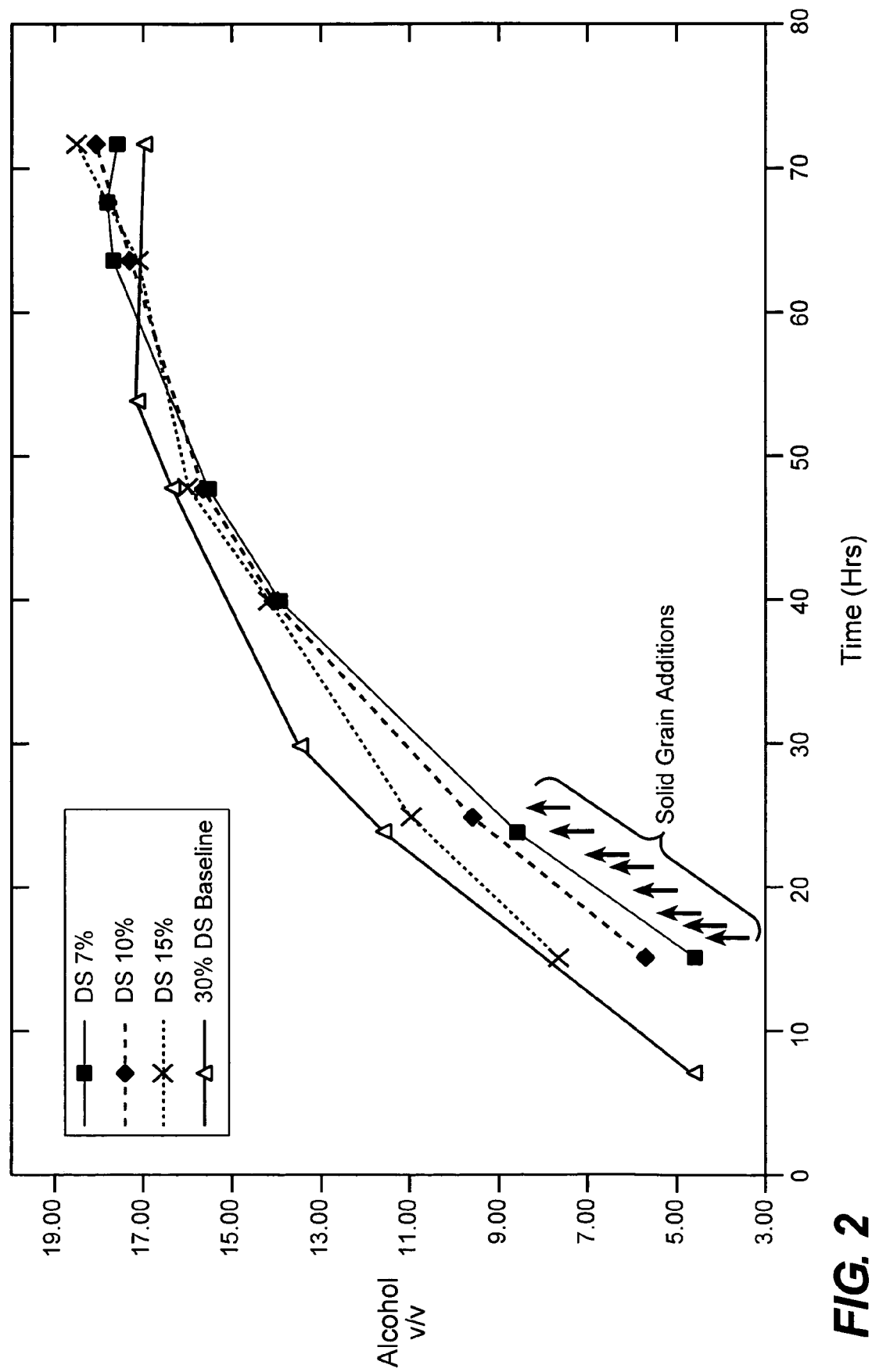
FIG. 2 illustrates the % (v/v) alcohol recovery from corn over time (hrs) at an initial dry solids (DS) of 7%, 10% and 15% with feeding of dry solid ground corn in the loading step at 1 hr intervals for 10 hrs beginning 15 hrs after the start of the initial fermentation step, wherein the accumulated DS was 30% and -■- represents an initial 7% DS; -♦- represents an initial 10% DS, -X- represents an initial 15% DS, and -Δ- represents the baseline 30% DS which was added at the beginning of the fermentation. Reference is made to example 3.

As observed from Tables 3A-D a steady increase in the final ethanol yield resulted from the higher initial staring DS with repetitive feeding of dry corn substrate compared to the 30% DS control. At 72 hours the % v/v ethanol was 17.06 for 30% DS (Table 3A); 17.57 for 7% DS (Table 3B); 18.11 for 10% DS (Table 3C); and 18.50 for 15% DS (Table 3D). Also reference is made to FIG. 2.

Example 4

Dry Solids Loading and Effect of Starting Time

Fermentations were carried out as described above in example 1 using different starting times for feeding the dry grain during the loading step after an initial fermentation time of 10 and 15 hours. The initial DS was 10%. The dry ground corn was added in equal weight at one-hour intervals for either 15 hours in the case of initial fermentation being 10 hours or 10 hours in the case of the initial fermentation being 15 hours. The final accumulated DS of the fermentation was 30% DS. In each case, the pH of the fermentation was adjusted to pH 4.7 using 26% sulphuric acid. The fermentation broth was sampled at 15, 24, 40, 48, 64 and 72 hours of total fermentation time by HPLC and the residual starch content was determined using the fermentation broth sampled from 72 hours.

TABLE 4A

Initial fermentation time 10 hours and feeding for 15 hours during the loading step

| Hour Sampled | DP > 2 % w/v | DP-2 % w/v | DP-1 % w/v | Lactic Acid % w/v | Glycerol % w/v | Ethanol % v/v |
|---|---|---|---|---|---|---|
| 15 | 0.13 | 0.03 | 0.17 | 0.09 | 0.72 | 7.68 |
| 24 | 0.28 | 0.04 | 0.49 | 0.11 | 0.94 | 10.97 |
| 40 | 0.28 | 0.04 | 1.25 | 0.12 | 1.01 | 14.19 |
| 48 | 0.31 | 0.06 | 1.04 | 0.12 | 1.12 | 16.01 |
| 64 | 0.25 | 0.07 | 0.35 | 0.11 | 1.19 | 17.17 |
| 72 | 0.35 | 0.11 | 0.47 | 0.12 | 1.27 | 18.50 |

TABLE 4B

Initial fermentation time 15 hours and feeding for 10 hours during the loading step

| Hour Sampled | DP > 2 % w/v | DP-2 % w/v | DP-1 % w/v | Lactic Acid % w/v | Glycerol % w/v | Ethanol % v/v |
|---|---|---|---|---|---|---|
| 15 | 0.16 | 0.02 | 0.07 | 0.10 | 0.88 | 7.76 |
| 24 | 0.26 | 0.02 | 0.13 | 0.13 | 0.99 | 10.75 |
| 40 | 0.30 | 0.05 | 1.22 | 0.15 | 1.12 | 14.51 |
| 48 | 0.27 | 0.05 | 1.08 | 0.14 | 1.15 | 15.48 |
| 64 | 0.23 | 0.09 | 0.47 | 0.14 | 1.14 | 17.42 |
| 72 | 0.28 | 0.06 | 0.22 | 0.15 | 1.21 | 17.78 |

The results as indicated in Tables 4A and B demonstrate the influence of the starting time on alcohol yield.

Example 5

Dry Solids Staging—Dry Ground Feeding with Different Grains

Fermentations were carried out as described in example 1 using different grain substrates. Corn, milo and wheat were subjected to a laboratory hammer mill 3100 (Sweden) using a 1.5 mm screen. More than 95% of the ground material passed through a 30 mesh screen. Rye and barley were purchased from Azure Standard (Dufur, Oreg.). The moisture content of the grains was measured using OHAUS, MB 35 Haolgen moisture balance (NJ). In a fermenter, 180-183 g (based on moisture content) of the ground grain and 950 g of water were combined along with 600 mg urea. The pH of the slurry was adjusted to pH 4.0 using 6N sulphuric acid. AnGA/AkAA was added at 1.0 GAU/g DS based on a final DS of 32% for each fermentation along with GC106 (Genencor International, Inc.) 0.5 Kgs/MT. Other secondary enzymes were added as follows: for wheat, CELLULASE 2000L (Genencor International Inc.) at 0.1 Kgs/MT; for barley, CELLULASE 2000L (Genencor International Inc.) at 0.5 Kgs/MT; and for rye, OTIMASH BG (Genencor International, Inc.) at 0.5 Kgs/MT. The fermenter was inoculated with 1.5 grams of dry RED STAR ETHANOL RED yeast (Lesafire Yeast Corp., Wis.). The fermentation medium was constantly mixed with a slow agitation at 30° C. The dry ground grain (122 grams each) was added in stepwise manner after 14 hours, 20 hours and 24 hours after the start of the initial fermentation. In each case the pH of the fermentation was adjusted to pH 4.0 using either 6 N $H_2SO_4$ or 2N KOH. Another dose of dry yeast, (1.5 grams) was added to each fermentation at 24 hours. The samples were taken at 14, 24, 48 and 72 hours and analyzed by HPLC. As observed in Table 5, the percent ethanol is produced for the tested grains vary and this variation is a function of the starch content of each grain type. For example it would be expected that the % ethanol yield from wheat at 72 hours would be less than the ethanol yield from corn at 72 hours. The residual starch content was determined using the fermenter broth sample from 72 hours.

TABLE 5

Effect of dry solids staging fermentation on ethanol production with different grain substrates

| Grain | Sample time (hrs) | % w/v DP > 2 | % w/v DP-2 | % w/v DP-1 | % w/v Lactic Acid | % w/v Glycerol | % v/v Ethanol |
|---|---|---|---|---|---|---|---|
| Corn | 14 | 0.79 | 0.01 | 0.01 | 0.03 | 0.32 | 4.95 |
|  | 24 | 0.37 | 0.00 | 0.04 | 0.06 | 0.50 | 8.71 |
|  | 49 | 0.43 | 0.00 | 0.03 | 0.09 | 0.84 | 16.72 |
|  | 72 | 0.39 | 0.00 | 0.00 | 0.03 | 0.88 | 17.76 |
| Milo | 14 | 0.26 | 0.02 | 0.01 | 0.03 | 0.37 | 5.15 |
|  | 24 | 0.40 | 0.00 | 0.04 | 0.07 | 0.59 | 9.17 |
|  | 49 | 0.47 | 0.00 | 0.03 | 0.10 | 0.96 | 17.48 |
|  | 72 | 0.46 | 0.00 | 0.00 | 0.06 | 0.99 | 17.83 |
| Wheat | 14 | 0.40 | 0.00 | 0.00 | 0.01 | 0.15 | 2.43 |
|  | 24 | 1.03 | 0.00 | 0.02 | 0.02 | 0.24 | 4.75 |
|  | 49 | 1.06 | 0.01 | 0.00 | 0.22 | 0.29 | 8.00 |
|  | 72 | 0.97 | 0.00 | 0.00 | 0.49 | 0.32 | 9.41 |
| Barely | 14 | 0.50 | 0.52 | 2.36 | 0.00 | 0.11 | 1.24 |
|  | 24 | 1.50 | 0.45 | 0.06 | 0.03 | 0.25 | 5.51 |

TABLE 5-continued

Effect of dry solids staging fermentation on ethanol production with different grain substrates

| Grain | Sample time (hrs) | % w/v DP > 2 | % w/v DP-2 | % w/v DP-1 | % w/v Lactic Acid | % w/v Glycerol | % v/v Ethanol |
|---|---|---|---|---|---|---|---|
| | 49 | 1.16 | 0.06 | 0.00 | 0.06 | 0.35 | 10.83 |
| | 72 | 1.04 | 0.00 | 0.02 | 0.07 | 0.43 | 12.39 |
| Rye | 14 | 1.01 | 0.04 | 0.00 | 0.03 | 0.00 | 3.56 |
| | 24 | 2.10 | 0.10 | 0.00 | 0.03 | 0.27 | 5.95 |
| | 49 | 2.07 | 0.05 | 0.00 | 0.05 | 0.38 | 10.11 |
| | 72 | 1.78 | 0.00 | 0.00 | 0.07 | 0.41 | 11.03 |

Example 6

Dry Solids Staging Compared to Batch Fermentation Using Fractionated Corn Endosperm A sample of #2 Yellow Dent corn was fractionated to obtain an endosperm fraction from the University of Illinois using known methods. The endosperm/gluten fraction was ground and a sample was obtained wherein at least 95% of the sample passed through a 1.5 mm screen (Perten Laboratory Mill 3100, Sweden). The moisture content of the grain was measured using an OHAUS, MB 35 Halogen moisture balance (NJ).

For the batch process, 483 grams of endosperm plus 1017 grams of DI water were used. For the dry solids staging (Dss) process, 161 grams of endosperm plus 1017 grams of DI water were used. At 14, 20 and 24 hours into the fermentation, 107 grams of endosperm per time period was added to the dry solids staging samples to obtain an accumulated DS of 30%. The pHs were adjusted to 4.0 using 6N $H_2SO_4$. The samples were placed into a 30° C. water bath and allowed to equilibrate. Additions of AnGA/AkAA at 1.0 GAU/g DS, GC106 (Genencor) at 0.5 Kgs/MT, and 1.5 g of RED STAR RED yeast (Lesaffre Yeast Corp. Wis.) were made to each sample. pH was monitored and adjusted to pH 4.0 using 4 N KOH if needed. Samples were taken at 14, 24, 38, 46, and 70 hours and analyzed by HPLC (Phenomenex rezex 8u). The residual starch content was determine using the fermentation broth after 72 hours.

batch process. These values demonstrate the higher carbon conversion efficiency of the dry solids staging process.

Example 7

Dry Solids Staging Fermentation Using Wet Milled Cereal Grain

A sample of #2 Yellow Dent corn was ground so that at least 95% of the sample passed through a 1.5 mm screen (Perten Laboratory Mill 3100, Sweden). The moisture content of the grain was measured using an OHAUS, MB 35 Halogen moisture balance (NJ). Initial fermentation was started with 750 g 10% DS ground corn. Urea (400 ppm) and 5.0 g of dried corn steep liquor were added to the flasks, and the pH was adjusted to pH 4.9 using 6 N $H_2SO_4$. The samples were placed in a 30° C. water bath and allowed to equilibrate. To start the fermentation, both 1.5 g RED STAR RED yeast (Lesaffre Yeast Corp. Wis.) and 1.0 GAU/g DS as AnGA-AkAA (Genencor) were added to each the flask. After 8 hours of the initial fermentation step, an additional 750 g of a starch slurry (34.7% DS) from a wet milled system was continuously added from a peristaltic pump (Gilson, Minipuls 3, Model M312, France) at a rate of 0.05 mls/min until the sample reached 1500 g total. The pH was monitored through out the experiment and was adjusted to 4.0 using 4N KOH if needed. Samples of mash were taken at 24, 32, 48, 56 and 70 hours and analyzed by HPLC (Phenomenex Rezex 8u). Residual starch content was determined using the fermenter broth sample after 70 hours. The results are illustrated in Table 7.

TABLE 6

| Process | Time (hr) | % w/v DP-1 | % w/v Lactic | % w/v Glycerol | % w/v Acetic | % v/v Ethanol | % Residual starch |
|---|---|---|---|---|---|---|---|
| Batch | 14 | 0.68 | 0.03 | 0.50 | 0.01 | 8.05 | |
| Dss | 14 | 0.71 | 0.02 | 0.35 | 0.00 | 4.97 | |
| Batch | 24 | 0.63 | 0.04 | 0.69 | 0.01 | 12.55 | |
| Dss | 24 | 0.71 | 0.03 | 0.54 | 0.00 | 9.04 | |
| Batch | 38 | 0.53 | 0.04 | 0.85 | 0.02 | 16.61 | |
| Dss | 38 | 0.90 | 0.04 | 0.77 | 0.01 | 14.98 | |
| Batch | 46 | 0.03 | 0.04 | 0.88 | 0.02 | 17.49 | |
| Dss | 46 | 0.62 | 0.04 | 0.83 | 0.02 | 16.53 | |
| Batch | 70 | 0.01 | 0.02 | 0.92 | 0.02 | 19.38 | 4.0 |
| Dss | 70 | 0.01 | 0.02 | 0.89 | 0.03 | 18.78 | 6.9 |

As Table 6 illustrates, during initial fermentation the rate of ethanol production is faster in the batch process due to higher levels of DS, but during the later stage of fermentation, the overall rate of ethanol production increases in the dry solids staging fermentation process. In addition, while the % residual starch in the dry solids staging fermentation process is higher than the batch process (6.9% as compared to 4.0% respectively), the % ethanol produced in the from the dry solids staging process is 18.78 as compared to 19.38 is the

TABLE 7

| Time (hr) | % w/v DP > 3 | % w/v DP-2 | % w/v DP-1 | % w/v Lactic | % w/v Glycerol | % v/v Ethanol |
|---|---|---|---|---|---|---|
| 24 | 0.24 | 0.02 | 0.93 | 0.10 | 0.48 | 5.18 |
| 32 | 0.26 | 0.02 | 1.60 | 0.10 | 0.58 | 6.72 |

TABLE 7-continued

| Time (hr) | % w/v DP > 3 | % w/v DP-2 | % w/v DP-1 | % w/v Lactic | % w/v Glycerol | % v/v Ethanol |
|---|---|---|---|---|---|---|
| 48 | 0.18 | 0.03 | 2.27 | 0.13 | 0.76 | 9.41 |
| 52 | 0.19 | 0.04 | 2.47 | 0.16 | 0.91 | 10.84 |
| 70 | 0.16 | 0.03 | 1.76 | 0.15 | 0.93 | 11.51 |

Example 8

Use of Liquefact in Dry Solids Staging Fermentation and Fed-Batch Fermentation

Liquefact was obtained from an ethanol produced and diluted down to 28% DS with DI water to obtain a one-liter sample. The pH of the sample was adjusted to pH 4.5 using 6N H$_2$SO$_4$. The sample was placed into a 30° C. water bath and allowed to equilibrate. 3.0 g RED STAR RED yeast (Lesaffre yeast Corp) and 0.4 GAU/g DS of DISTILLASE L-400 (Genencor), and 7 Spectrophotometric Acid protease Units (SAPU) of GC 106/g DS (Genencor) were added to the samples. One SAPU is the amount of enzyme activity that liberates one micromole of tyrosine per minute from a casein substrate under assay conditions. After 15 hours the mash was divided into 4 duplicate treatments each containing 100 g samples.

Treatment A continued through the fermentation without an additional loading step or additional dosing of enzyme or yeast. For treatment B, AnGA/AkAA at 1.0 GAU/g DS and 0.3 g of yeast were added based on an accumulated DS of 36% but no additional fermentable substrate was added. For treatment C, in addition to AnGA/AkAA at 1.0 GAU/g DS and 0.3 g of yeast, 15.4 g of ground corn was added in one feeding at the 15 hour time period. For treatment D, the ground corn was added at 15, 20 and 25 hours in equal increments of 5.1 g for a total of 15.4 g. The ground corn was produced using a 1.5 mm screen and a laboratory Hammer Mill 3100 (Sweden). More than 95% of the ground corn passed through a 30 mesh screen. The moisture content of the grain was measured using an OHAUS MB 35 Halogen Moisture Balance. The accumulated DS for both treatments C and D was 36%.

Mash samples were taken at 24, 36, 48, and 72 hours and analyzed by HPLC (Phenomenex Rezex 8u) and the residual starch content was determined using the mash sample after 72 hours. The results are illustrated in Table 8.

TABLE 8

| Treatment | Time (hrs) | % w/v DP > 3 | % w/v DP-1 | % w/v Glycerol | % v/v Ethanol | % Residual Starch |
|---|---|---|---|---|---|---|
| A | 24 | 4.91 | 0.38 | 0.91 | 9.07 | |
| B | | 3.37 | 1.89 | 1.02 | 10.35 | |
| C | | 2.80 | 1.85 | 0.98 | 11.02 | |
| D | | 2.92 | 1.91 | 1.01 | 10.78 | |
| A | 36 | 1.96 | 0.58 | 0.99 | 11.45 | |
| B | | 0.62 | 0.08 | 1.10 | 12.93 | |
| C | | 0.54 | 0.44 | 1.14 | 14.17 | |
| D | | 0.49 | 0.46 | 1.15 | 14.02 | |
| A | 48 | 1.36 | 0.09 | 1.03 | 12.85 | |
| B | | 0.86 | 0.05 | 1.07 | 13.12 | |
| C | | 0.88 | 0.93 | 1.13 | 14.62 | |
| D | | 0.81 | 0.83 | 1.12 | 14.47 | |
| A | 72 | 1.01 | 0.05 | 1.04 | 13.29 | 1.86 |
| B | | 0.78 | 0.04 | 1.07 | 13.33 | 1.24 |
| C | | 0.88 | 2.15 | 1.22 | 16.39 | 12.33 |
| D | | 0.87 | 2.17 | 1.19 | 16.34 | 14.40 |

The results reported in Table 8 illustrate the higher carbon conversion efficiency of the dry solids staging fermentation process. For treatments C and D, which are representative of the dry solids staging process, the % ethanol at 72 hours was 16.39% and 16.34%, respectively compared with 13.29% and 13.33% ethanol production for treatments A and B. The % residual starch for treatments C and D were 12.33% and 14.40% respectively, while the % residual starch for treatments A and B were only 1.86% and 1.24%.

It is claimed:

1. A dry solids staging fermentation process for producing ethanol comprising:
   a) an initial fermentation step which includes directly feeding a dry ground cereal grain into a fermentation vessel, combining therein the dry ground cereal grain with one or more starch hydrolyzing enzymes and a fermenting organism at a pH of 3.0 to 6.0, a temperature of 5 to 65° C. for an initial period of 2 to 40 hours, and obtaining a fermentation broth having an initial percent dry solids (% DS) of 15 to 30%;
   b) a loading step which includes adding a solid fermentable substrate into the fermentation vessel after the initial period of 2 to 40 hours and allowing continued fermentation at a pH of 3.0 to 6.0, at a temperature of 20 to 55° C. for a sufficient period of time to produce ethanol, wherein accumulated % DS of the fermentation broth increases over time and is between 30 to 40%, wherein the accumulated % DS is at least 5% greater than the initial % DS, and wherein the dry solids staging fermentation process is conducted for a total of 24 to 108 hours; and
   c) recovering the ethanol produced in step b), wherein the yield of ethanol is at least 14% v/v.

2. The dry solids staging fermentation process according to claim 1, wherein the solid fermentable substrate is directly fed into the fermentation vessel.

3. The dry solids staging fermentation process according to claim 1, wherein the cereal grain is selected from the group consisting of corn, rye, wheat, barley, milo or combinations thereof.

4. The dry solids staging fermentation process according to claim 3, wherein the grain has been fractionated.

5. The dry solids staging fermentation process according to claim 1, wherein the initial fermentation step continues for at least 5 hours before the loading step.

6. The dry solids staging fermentation process according to claim 1, wherein the one or more starch hydrolyzing enzymes are selected from the group of glucoamylases, alpha amylases, enzymes having granular starch hydrolyzing activity and combinations thereof.

7. The dry solids staging fermentation process according to claim 1, wherein the one or more starch hydrolyzing enzymes is a glucoamylase.

8. The dry solids staging fermentation process according to claim 1, wherein the one or more starch hydrolyzing enzymes is an enzyme having granular starch hydrolyzing activity.

9. The dry solids staging fermentation process according to claim 1, wherein the one or more starch hydrolyzing enzymes includes a combination of a glucoamylase and a granular starch hydrolyzing enzyme.

10. The dry solids staging fermentation process according to claim 9, wherein the one or more starch hydrolyzing enzymes includes a combination of an *Aspergillus niger* glucoamylase and a fungal alpha amylase having granular starch hydrolyzing activity.

11. The dry solids staging fermentation process according to claim 1, further comprising the addition of secondary enzymes to either the initial fermentation step or the loading step.

12. The dry solids staging fermentation process according to claim 11, wherein the secondary enzymes include proteases, amylases, pullulanases, cellulases or combinations thereof.

13. The dry solids staging fermentation process according to claim 1, further comprising recovering co-products from the fermentation broth.

14. The dry solids staging fermentation process according to claim 13, wherein the co-products are distillers dried grain or distillers dried grain with solubles.

15. The dry solids staging fermentation process according to claim 14, wherein the distillers dried grain with solubles has a residual starch content of less than 20%.

16. The dry solids staging fermentation process according to claim 1, wherein the process is conducted for a total of 30 to 92 hours.

17. The dry solids staging process according to claim 1, wherein the initial fermentation step is conducted at pH 3.5 to 5.5, a temperature of 25° C. to 45° C., for 2 to 10 hours and the dry ground cereal grain is combined with at least one granular starch hydrolyzing enzyme and yeast in the fermentation vessel.

18. The dry solids staging fermentation process according to claim 17, wherein the dry ground cereal grain is corn, rye, wheat, barely, milo or combinations thereof.

19. The dry solids staging fermentation process according to claim 1, wherein the fermentation broth is constantly mixed with slow agitation.

20. A dry solids staging fermentation process for producing ethanol comprising:
   a) an initial fermentation step comprising directly feeding milled corn grain into a fermentation vessel and combining therein the milled corn grain with an alpha amylase, a glucoamylase and yeast at a pH of 3.0 to 7.0, a temperature of 10 to 65° C., for an initial period of 2 to 40 hours, and obtaining a fermentation broth;
   b) a loading step comprising adding a fermentable substrate into the fermentation vessel which contains the fermentation broth after the initial period of 2 to 40 hours and allowing continued fermentation at a pH of 3.0 to 7.0, a temperature of between 20 to 65° C. for a sufficient period of time to produce ethanol, wherein the percent dry solids (% DS) of the fermentation broth has an initial percent dry solids (% DS) of 15 to 30% that increases over time to between 30 to 40%; and
   c) recovering the ethanol produced in step b),
   wherein the dry solids staging fermentation process is conducted for a total of between 30 to 92 hours and the yield of ethanol is at least 14% v/v.

21. The dry solids staging process according to claim 20, wherein the corn is fractionated.

22. The dry solids staging fermentation process according to claim 20, wherein the fermentation broth is constantly mixed with slow agitation.

\* \* \* \* \*

SEQUENCE LISTING

```
<160> NUMBER OF SEQ ID NOS: 3

<210> SEQ ID NO 1
<211> LENGTH: 604
<212> TYPE: PRT
<213> ORGANISM: Humicola grisea var. thermoidea

<400> SEQUENCE: 1

Ala Ala Val Asp Thr Phe Ile Asn Thr Glu Lys Pro Ile Ala Trp Asn
1               5                   10                  15

Lys Leu Leu Ala Asn Ile Gly Pro Asn Gly Lys Ala Ala Pro Gly Ala
            20                  25                  30

Ala Ala Gly Val Val Ile Ala Ser Pro Ser Arg Thr Asp Pro Pro Tyr
        35                  40                  45

Phe Phe Thr Trp Thr Arg Asp Ala Ala Leu Val Leu Thr Gly Ile Ile
    50                  55                  60

Glu Ser Leu Gly His Asn Tyr Asn Thr Thr Leu Gln Thr Val Ile Gln
65                  70                  75                  80

Asn Tyr Val Ala Ser Gln Ala Lys Leu Gln Gln Val Ser Asn Pro Ser
                85                  90                  95

Gly Thr Phe Ala Asp Gly Ser Gly Leu Gly Glu Ala Lys Phe Asn Val
            100                 105                 110
```

-continued

```
Asp Leu Thr Ala Phe Thr Gly Glu Trp Gly Arg Pro Gln Arg Asp Gly
            115                 120                 125

Pro Pro Leu Arg Ala Ile Ala Leu Ile Gln Tyr Ala Lys Trp Leu Ile
130                 135                 140

Ala Asn Gly Tyr Lys Ser Thr Ala Lys Ser Val Val Trp Pro Val Val
145                 150                 155                 160

Lys Asn Asp Leu Ala Tyr Thr Ala Gln Tyr Trp Asn Glu Thr Gly Phe
                165                 170                 175

Asp Leu Trp Glu Glu Val Pro Gly Ser Ser Phe Phe Thr Ile Ala Ser
            180                 185                 190

Ser His Arg Ala Leu Thr Glu Gly Ala Tyr Leu Ala Ala Gln Leu Asp
        195                 200                 205

Thr Glu Cys Arg Ala Cys Thr Thr Val Ala Pro Gln Val Leu Cys Phe
    210                 215                 220

Gln Gln Ala Phe Trp Asn Ser Lys Gly Asn Tyr Val Val Ser Asn Ile
225                 230                 235                 240

Asn Gly Gly Glu Tyr Arg Ser Gly Lys Asp Ala Asn Ser Ile Leu Ala
                245                 250                 255

Ser Ile His Asn Phe Asp Pro Glu Ala Gly Cys Asp Asn Leu Thr Phe
            260                 265                 270

Gln Pro Cys Ser Glu Arg Ala Leu Ala Asn His Lys Ala Tyr Val Asp
        275                 280                 285

Ser Phe Arg Asn Leu Tyr Ala Ile Asn Lys Gly Ile Ala Gln Gly Lys
    290                 295                 300

Ala Val Ala Val Gly Arg Tyr Ser Glu Asp Val Tyr Tyr Asn Gly Asn
305                 310                 315                 320

Pro Trp Tyr Leu Ala Asn Phe Ala Ala Ala Glu Gln Leu Tyr Asp Ala
                325                 330                 335

Ile Tyr Val Trp Asn Lys Gln Gly Ser Ile Thr Val Thr Ser Val Ser
            340                 345                 350

Leu Pro Phe Phe Arg Asp Leu Val Ser Ser Val Ser Thr Gly Thr Tyr
        355                 360                 365

Ser Lys Ser Ser Ser Thr Phe Thr Asn Ile Val Asn Ala Val Lys Ala
    370                 375                 380

Tyr Ala Asp Gly Phe Ile Glu Val Ala Ala Lys Tyr Thr Pro Ser Asn
385                 390                 395                 400

Gly Ala Leu Ala Glu Gln Tyr Asp Arg Asn Thr Gly Lys Pro Asp Ser
                405                 410                 415

Ala Ala Asp Leu Thr Trp Ser Tyr Ser Ala Phe Leu Ser Ala Ile Asp
            420                 425                 430

Arg Arg Ala Gly Leu Val Pro Pro Ser Trp Arg Ala Ser Val Ala Lys
        435                 440                 445

Ser Gln Leu Pro Ser Thr Cys Ser Arg Ile Glu Val Ala Gly Thr Tyr
    450                 455                 460

Val Ala Ala Thr Ser Thr Ser Phe Pro Ser Lys Gln Thr Pro Asn Pro
465                 470                 475                 480

Ser Ala Ala Pro Ser Pro Ser Pro Tyr Pro Thr Ala Cys Ala Asp Ala
                485                 490                 495

Ser Glu Val Tyr Val Thr Phe Asn Glu Arg Val Ser Thr Ala Trp Gly
            500                 505                 510

Glu Thr Ile Lys Val Val Gly Asn Val Pro Ala Leu Gly Asn Trp Asp
        515                 520                 525

Thr Ser Lys Ala Val Thr Leu Ser Ala Ser Gly Tyr Lys Ser Asn Asp
```

-continued

```
            530                 535                 540
Pro Leu Trp Ser Ile Thr Val Pro Ile Lys Ala Thr Gly Ser Ala Val
545                 550                 555                 560

Gln Tyr Lys Tyr Ile Lys Val Gly Thr Asn Gly Lys Ile Thr Trp Glu
                565                 570                 575

Ser Asp Pro Asn Arg Ser Ile Thr Leu Gln Thr Ala Ser Ser Ala Gly
                580                 585                 590

Lys Cys Ala Ala Gln Thr Val Asn Asp Ser Trp Arg
                595                 600

<210> SEQ ID NO 2
<211> LENGTH: 615
<212> TYPE: PRT
<213> ORGANISM: Aspergillus awamori var. kawachi

<400> SEQUENCE: 2

Ala Thr Leu Asp Ser Trp Leu Ser Asn Glu Ala Thr Val Ala Arg Thr
1               5                   10                  15

Ala Ile Leu Asn Asn Ile Gly Ala Asp Gly Ala Trp Val Ser Gly Ala
                20                  25                  30

Asp Ser Gly Ile Val Val Ala Ser Pro Ser Thr Asp Asn Pro Asp Tyr
            35                  40                  45

Phe Tyr Thr Trp Thr Arg Asp Ser Gly Leu Val Ile Lys Thr Leu Val
50                  55                  60

Asp Leu Phe Arg Asn Gly Asp Thr Asp Leu Leu Ser Thr Ile Glu His
65                  70                  75                  80

Tyr Ile Ser Ser Gln Ala Ile Ile Gln Gly Val Ser Asn Pro Ser Gly
                85                  90                  95

Asp Leu Ser Ser Gly Gly Leu Gly Glu Pro Lys Phe Asn Val Asp Glu
            100                 105                 110

Thr Ala Tyr Thr Gly Ser Trp Gly Arg Pro Gln Arg Asp Gly Pro Ala
            115                 120                 125

Leu Arg Ala Thr Ala Met Ile Gly Phe Gly Gln Trp Leu Leu Asp Asn
130                 135                 140

Gly Tyr Thr Ser Ala Ala Thr Glu Ile Val Trp Pro Leu Val Arg Asn
145                 150                 155                 160

Asp Leu Ser Tyr Val Ala Gln Tyr Trp Asn Gln Thr Gly Tyr Asp Leu
                165                 170                 175

Trp Glu Glu Val Asn Gly Ser Ser Phe Phe Thr Ile Ala Val Gln His
            180                 185                 190

Arg Ala Leu Val Glu Gly Ser Ala Phe Ala Thr Ala Val Gly Ser Ser
            195                 200                 205

Cys Ser Trp Cys Asp Ser Gln Ala Pro Gln Ile Leu Cys Tyr Leu Gln
210                 215                 220

Ser Phe Trp Thr Gly Ser Tyr Ile Leu Ala Asn Phe Asp Ser Ser Arg
225                 230                 235                 240

Ser Gly Lys Asp Thr Asn Thr Leu Leu Gly Ser Ile His Thr Phe Asp
                245                 250                 255

Pro Glu Ala Gly Cys Asp Asp Ser Thr Phe Gln Pro Cys Ser Pro Arg
            260                 265                 270

Ala Leu Ala Asn His Lys Glu Val Val Asp Ser Phe Arg Ser Ile Tyr
            275                 280                 285

Thr Leu Asn Asp Gly Leu Ser Asp Ser Glu Ala Val Ala Val Gly Arg
            290                 295                 300
```

Tyr Pro Glu Asp Ser Tyr Asn Gly Asn Pro Trp Phe Leu Cys Thr
305                 310                 315                 320

Leu Ala Ala Glu Gln Leu Tyr Asp Ala Leu Tyr Gln Trp Asp Lys
            325                 330                 335

Gln Gly Ser Leu Glu Ile Thr Asp Val Ser Leu Asp Phe Phe Lys Ala
            340                 345                 350

Leu Tyr Ser Gly Ala Ala Thr Gly Thr Tyr Ser Ser Ser Ser Thr
            355                 360                 365

Tyr Ser Ser Ile Val Ser Ala Val Lys Thr Phe Ala Asp Gly Phe Val
370                 375                 380

Ser Ile Val Glu Thr His Ala Ala Ser Asn Gly Ser Leu Ser Glu Gln
385                 390                 395                 400

Phe Asp Lys Ser Asp Gly Asp Glu Leu Ser Ala Arg Asp Leu Thr Trp
            405                 410                 415

Ser Tyr Ala Ala Leu Leu Thr Ala Asn Asn Arg Arg Asn Ser Val Val
            420                 425                 430

Pro Pro Ser Trp Gly Glu Thr Ser Ala Ser Ser Val Pro Gly Thr Cys
        435                 440                 445

Ala Ala Thr Ser Ala Ser Gly Thr Tyr Ser Ser Val Thr Val Thr Ser
450                 455                 460

Trp Pro Ser Ile Val Ala Thr Gly Gly Thr Thr Thr Thr Ala Thr Thr
465                 470                 475                 480

Thr Gly Ser Gly Gly Val Thr Ser Thr Ser Lys Thr Thr Thr Thr Ala
            485                 490                 495

Ser Lys Thr Ser Thr Thr Thr Ser Ser Thr Ser Cys Thr Thr Pro Thr
            500                 505                 510

Ala Val Ala Val Thr Phe Asp Leu Thr Ala Thr Thr Thr Tyr Gly Glu
            515                 520                 525

Asn Ile Tyr Leu Val Gly Ser Ile Ser Gln Leu Gly Asp Trp Glu Thr
530                 535                 540

Ser Asp Gly Ile Ala Leu Ser Ala Asp Lys Tyr Thr Ser Ser Asn Pro
545                 550                 555                 560

Leu Trp Tyr Val Thr Val Thr Leu Pro Ala Gly Glu Ser Phe Glu Tyr
            565                 570                 575

Lys Phe Ile Arg Val Glu Ser Asp Asp Ser Val Glu Trp Glu Ser Asp
            580                 585                 590

Pro Asn Arg Glu Tyr Thr Val Pro Gln Ala Cys Gly Glu Ser Thr Ala
            595                 600                 605

Thr Val Thr Asp Thr Trp Arg
610                 615

<210> SEQ ID NO 3
<211> LENGTH: 619
<212> TYPE: PRT
<213> ORGANISM: Aspergillus awamori var. kawachi

<400> SEQUENCE: 3

Leu Ser Ala Ala Glu Trp Arg Thr Gln Ser Ile Tyr Phe Leu Leu Thr
1               5                   10                  15

Asp Arg Phe Gly Arg Thr Asp Asn Ser Thr Thr Ala Thr Cys Asn Thr
            20                  25                  30

Gly Asp Gln Ile Tyr Cys Gly Gly Ser Trp Gln Gly Ile Ile Asn His
        35                  40                  45

Leu Asp Tyr Ile Gln Gly Met Gly Phe Thr Ala Ile Trp Ile Ser Pro
50                  55                  60

-continued

```
Ile Thr Glu Gln Leu Pro Gln Asp Thr Ser Asp Gly Glu Ala Tyr His
65                  70                  75                  80

Gly Tyr Trp Gln Gln Lys Ile Tyr Asn Val Asn Ser Asn Phe Gly Thr
                85                  90                  95

Ala Asp Asp Leu Lys Ser Leu Ser Asp Ala Leu His Ala Arg Gly Met
            100                 105                 110

Tyr Leu Met Val Asp Val Val Pro Asn His Met Gly Tyr Ala Gly Asn
        115                 120                 125

Gly Asn Asp Val Asp Tyr Ser Val Phe Asp Pro Phe Asp Ser Ser Ser
    130                 135                 140

Tyr Phe His Pro Tyr Cys Leu Ile Thr Asp Trp Asp Asn Leu Thr Met
145                 150                 155                 160

Val Gln Asp Cys Trp Glu Gly Asp Thr Ile Val Ser Leu Pro Asp Leu
                165                 170                 175

Asn Thr Thr Glu Thr Ala Val Arg Thr Ile Trp Tyr Asp Trp Val Ala
            180                 185                 190

Asp Leu Val Ser Asn Tyr Ser Val Asp Gly Leu Arg Ile Asp Ser Val
        195                 200                 205

Glu Glu Val Glu Pro Asp Phe Phe Pro Gly Tyr Gln Glu Ala Ala Gly
    210                 215                 220

Val Tyr Cys Val Gly Glu Val Asp Asn Gly Asn Pro Ala Leu Asp Cys
225                 230                 235                 240

Pro Tyr Gln Lys Tyr Leu Asp Gly Val Leu Asn Tyr Pro Ile Tyr Trp
                245                 250                 255

Gln Leu Leu Tyr Ala Phe Glu Ser Ser Gly Ser Ile Ser Asn Leu
            260                 265                 270

Tyr Asn Met Ile Lys Ser Val Ala Ser Asp Cys Ser Asp Pro Thr Leu
        275                 280                 285

Leu Gly Asn Phe Ile Glu Asn His Asp Asn Pro Arg Phe Ala Ser Tyr
    290                 295                 300

Thr Ser Asp Tyr Ser Gln Ala Lys Asn Val Leu Ser Tyr Ile Phe Leu
305                 310                 315                 320

Ser Asp Gly Ile Pro Ile Val Tyr Ala Gly Glu Glu His Tyr Ser
                325                 330                 335

Gly Gly Asp Val Pro Tyr Asn Arg Glu Ala Thr Trp Leu Ser Gly Tyr
            340                 345                 350

Asp Thr Ser Ala Glu Leu Tyr Thr Trp Ile Ala Thr Asn Ala Ile
        355                 360                 365

Arg Lys Leu Ala Ile Ser Ala Asp Ser Asp Tyr Ile Thr Tyr Ala Asn
    370                 375                 380

Asp Pro Ile Tyr Thr Asp Ser Asn Thr Ile Ala Met Arg Lys Gly Thr
385                 390                 395                 400

Ser Gly Ser Gln Ile Ile Thr Val Leu Ser Asn Lys Gly Ser Ser Gly
                405                 410                 415

Ser Ser Tyr Thr Leu Thr Leu Ser Gly Ser Tyr Thr Ser Gly Thr
            420                 425                 430

Lys Leu Ile Glu Ala Tyr Thr Cys Thr Ser Val Thr Val Asp Ser Asn
        435                 440                 445

Gly Asp Ile Pro Val Pro Met Ala Ser Gly Leu Pro Arg Val Leu Leu
    450                 455                 460

Pro Ala Ser Val Val Asp Ser Ser Leu Cys Gly Gly Ser Gly Asn
465                 470                 475                 480
```

-continued

```
Thr Thr Thr Thr Thr Thr Ala Ala Thr Ser Thr Ser Lys Ala Thr Thr
            485             490             495

Ser Ser Ser Ser Ser Ala Ala Ala Thr Thr Ser Ser Ser Cys Thr
        500             505             510

Ala Thr Ser Thr Thr Leu Pro Ile Thr Phe Glu Glu Leu Val Thr Thr
        515             520             525

Thr Tyr Gly Glu Glu Val Tyr Leu Ser Gly Ser Ile Ser Gln Leu Gly
        530             535             540

Glu Trp Asp Thr Ser Asp Ala Val Lys Leu Ser Ala Asp Asp Tyr Thr
545             550             555             560

Ser Ser Asn Pro Glu Trp Ser Val Thr Val Ser Leu Pro Val Gly Thr
            565             570             575

Thr Phe Glu Tyr Lys Phe Ile Lys Val Asp Glu Gly Gly Ser Val Thr
            580             585             590

Trp Glu Ser Asp Pro Asn Arg Glu Tyr Thr Val Pro Glu Cys Gly Ser
        595             600             605

Gly Ser Gly Glu Thr Val Val Asp Thr Trp Arg
    610             615
```